US010786653B2

(12) United States Patent
Galgano et al.

(10) Patent No.: US 10,786,653 B2
(45) Date of Patent: Sep. 29, 2020

(54) CATHETER ASSEMBLY WITH SEGMENTED STABILIZATION SYSTEM

(71) Applicant: Bloodworks LLC, Rochester, MN (US)

(72) Inventors: Joshua J. Galgano, Silver Spring, MD (US); Hanjun Kim, Jr., Pittsburgh, PA (US); Robert J. Anderson, North Liberty, IA (US)

(73) Assignee: Bloodworks LLC, Rochester, MN (US)

( * ) Notice: Subject to any disclaimer, the term of this patent is extended or adjusted under 35 U.S.C. 154(b) by 1395 days.

(21) Appl. No.: 14/782,422

(22) PCT Filed: Apr. 4, 2014

(86) PCT No.: PCT/US2014/033012
§ 371 (c)(1),
(2) Date: Oct. 5, 2015

(87) PCT Pub. No.: WO2014/165783
PCT Pub. Date: Oct. 9, 2014

(65) Prior Publication Data
US 2016/0045715 A1 Feb. 18, 2016

Related U.S. Application Data

(60) Provisional application No. 61/808,982, filed on Apr. 5, 2013.

(51) Int. Cl.
*A61M 25/06* (2006.01)
*A61M 25/09* (2006.01)
*A61B 17/34* (2006.01)

(52) U.S. Cl.
CPC .... *A61M 25/0606* (2013.01); *A61M 25/0662* (2013.01); *A61M 25/09* (2013.01); *A61B 17/3403* (2013.01); *A61M 2025/0681* (2013.01)

(58) Field of Classification Search
None
See application file for complete search history.

(56) References Cited

U.S. PATENT DOCUMENTS 5,100,425 A * 3/1992 Fischell ......... A61B 17/320725
604/22
5,217,026 A * 6/1993 Stoy ................. A61M 25/0009
427/336

(Continued)

FOREIGN PATENT DOCUMENTS

WO 2008076917 A2 6/2008
WO 2011143621 A1 11/2011

OTHER PUBLICATIONS

International Searching Authority, "Search Report and Written Opinion", issued in connection with International Application No. PCT/US2014/033012, dated Aug. 7, 2014, 11 pages.

*Primary Examiner* — Rebecca E Eisenberg
*Assistant Examiner* — Weng Lee
(74) *Attorney, Agent, or Firm* — McKee, Voorhees & Sease, PLC

(57) ABSTRACT

A catheter assembly with segmented or step-wise deployment stabilization system includes a base or handle, puncture needle extending from the handle, and a deployment mechanism or mechanisms to selectively extend from the distal end of the needle for first length a hollow stabilizing component and as a second step to a second further length a stabilizing guide wire element. The needle will gain sub-dermal access to the patient to the intended position for deployment of a catheter. Hollow stabilizing component provides for a first additional guide and support for a catheter sheath from the distal end of the needle. The stabilizing wire element provides additional length, guide and support for the catheter sheath. The hollow stabilizing component has some degree of flexibility as does the guide (Continued)

wire to minimize chance of damage to surrounding tissue. The user can feel resistance and have the opportunity to retract either component and attempt redeployment without a retraction of the puncture needle and a second poke of the patient's skin. In the example for peripheral venous catheterization, the system reduces the probability of blood vessel puncture. The deployment mechanism can have a guiding system which ensures the proper sequence of deployment.

24 Claims, 25 Drawing Sheets

(56) References Cited

U.S. PATENT DOCUMENTS

| | | | |
|---|---|---|---|
| 5,279,590 A | 1/1994 | Sinko et al. | |
| 7,025,746 B2* | 4/2006 | Tal | A61M 25/0662 604/164.1 |
| 2002/0072720 A1* | 6/2002 | Hague | A61B 5/6849 604/264 |
| 2005/0033393 A1* | 2/2005 | Daglow | A61B 17/3415 607/116 |
| 2006/0095006 A1 | 5/2006 | Yang et al. | |
| 2007/0129682 A1* | 6/2007 | Eidenschink | A61M 25/09 604/164.13 |
| 2008/0300574 A1 | 12/2008 | Belson et al. | |
| 2009/0030380 A1 | 1/2009 | Binmoeller | |
| 2012/0238872 A1* | 9/2012 | Schwager | A61M 25/09 600/434 |

* cited by examiner

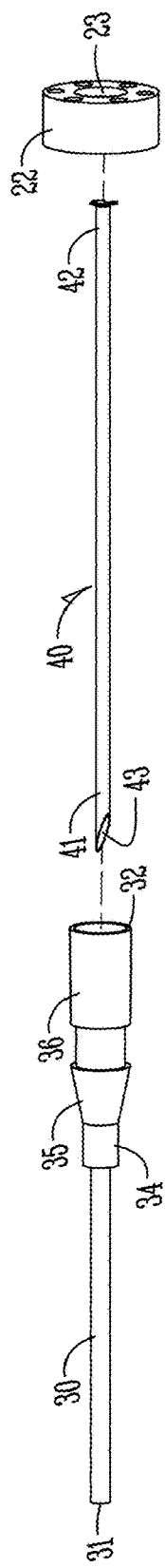
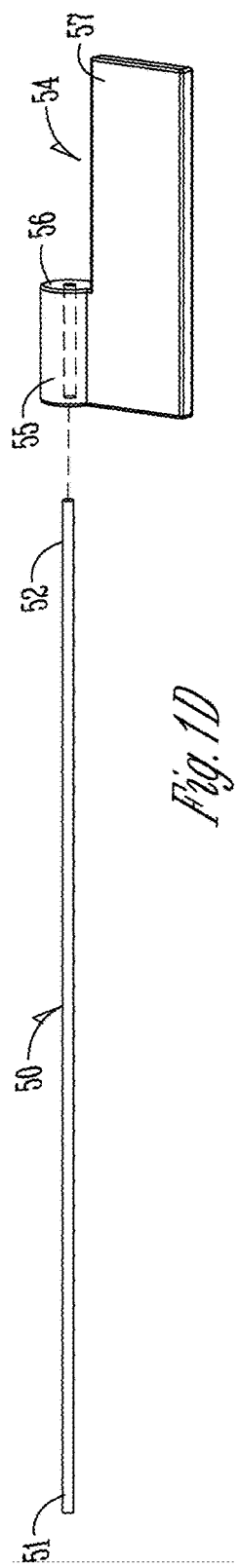
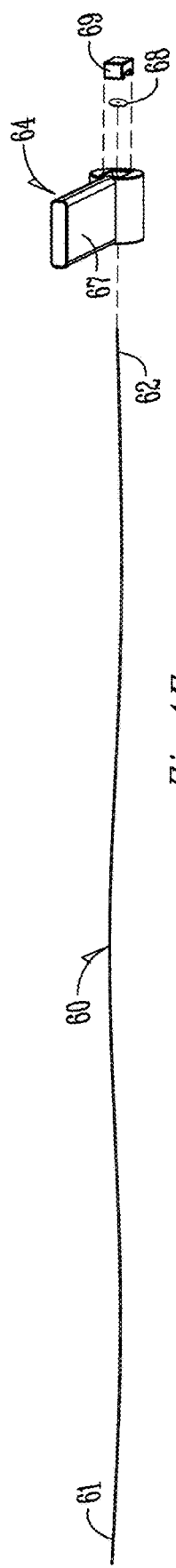
Fig. 1C
Fig. 1D
Fig. 1E

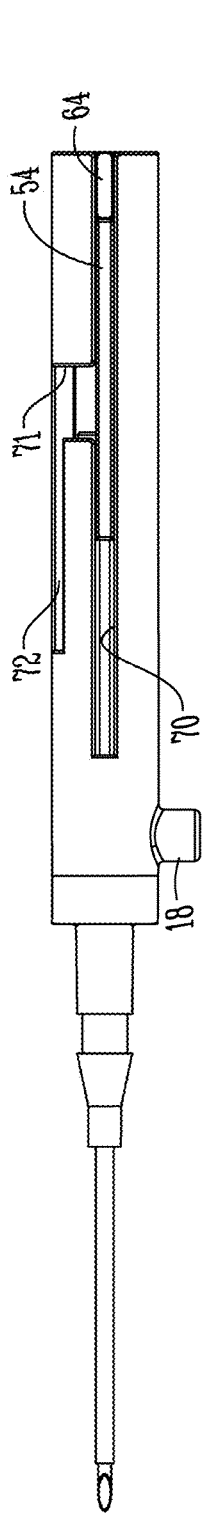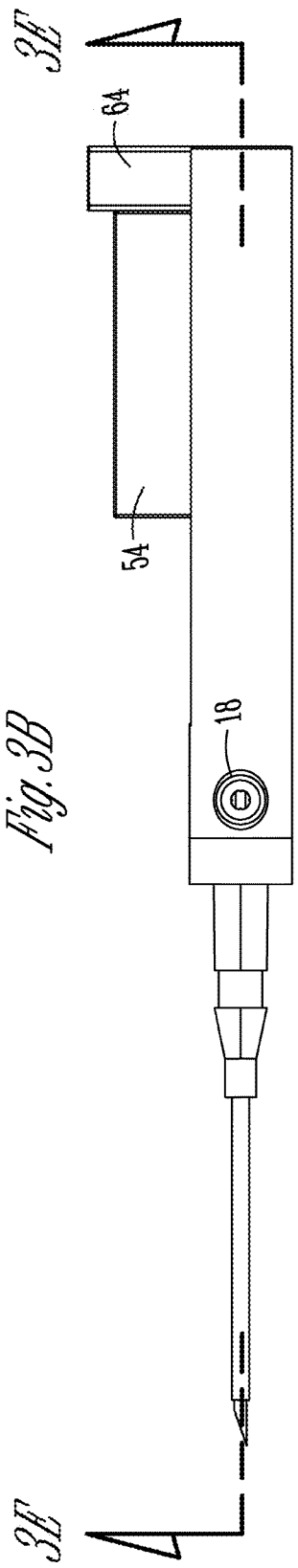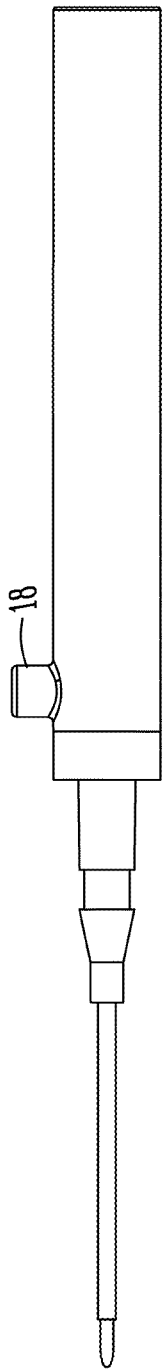

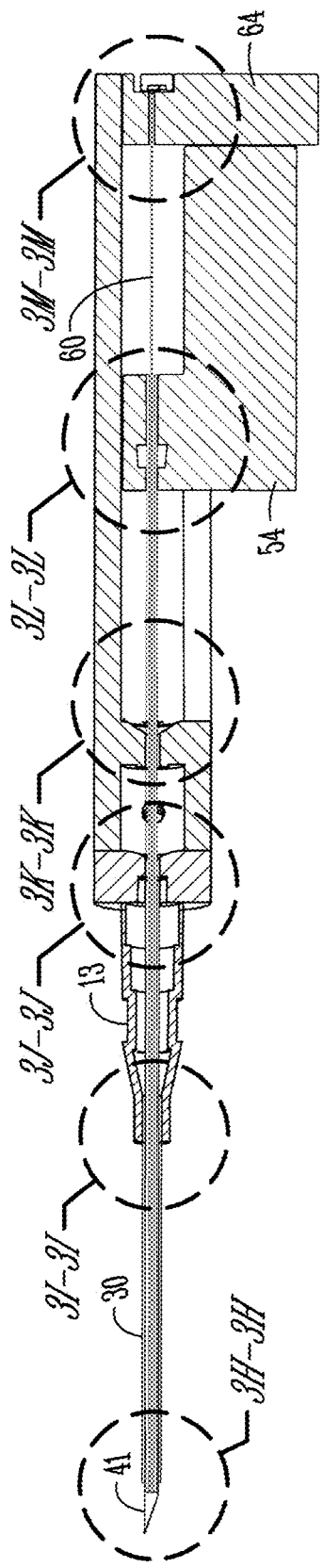
Fig. 3E
Fig. 3F
Fig. 3G

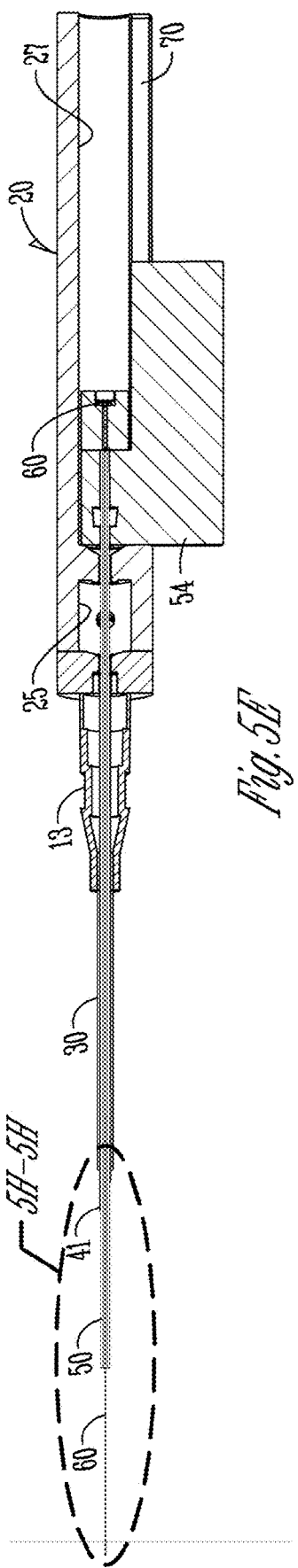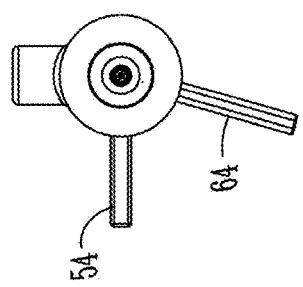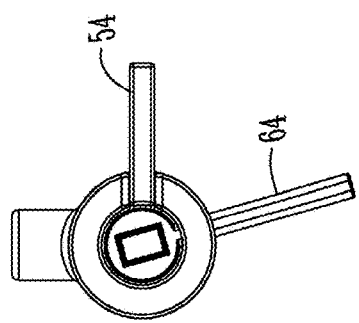
Fig. 5E
Fig. 5G
Fig. 5H

CATHETER ASSEMBLY WITH SEGMENTED STABILIZATION SYSTEM

CROSS-REFERENCE TO RELATED APPLICATIONS

This application claims the benefit of U.S. provisional application Ser. No. 61/808,982 filed Apr. 5, 2013 and PCT application serial No. PCT/US/2014/033012 filed Apr. 4, 2014, both of which are incorporated by reference in their entireties.

FIELD OF INVENTION

The present invention relates generally to the field of catheters and methods of using the same. More particularly, but not exclusively, it is a method for facilitating the insertion of a peripheral intravascular catheter into a vein or artery by using a hollow stabilizing component through which another component, one example being a thin guide wire, is passed. Subsequently, the method allows for a catheter sheath to pass over the hollow stabilizing component and any additional components such as a thin guide wire, emplacing the catheter within the patient's vessel.

RELATED ART

Peripheral intravascular catheters are ubiquitous in hospitals and medical centers throughout the world. Many of these devices are wasted due to failure to properly cannulate or thread the catheter into the vein. Furthermore, the procedure varies in difficulty depending on the condition of the patient. For example, patients suffering from dehydration or other illnesses typically lack straight and/or plump superficial veins which are ideal for peripheral vessel cannulation. Such substandard veins are difficult to find, and maneuvering a needle within them is arduous. However, arterial line catheters currently used in practice are easier to place/cannulate through the aid of a guide wire that passes through the needle upon entering the blood vessel. The Seldinger technique, as it is called and is known in this field of endeavor, uses the guide wire to position itself within the vessel after which it acts as a support for the catheter sheath to be slid over it. With the catheter fixed and in place, the guide wire is then removed. The catheter is then available for use.

Applying the Seldinger technique to a peripheral intravenous catheter can be advantageous in facilitating catheter insertion. However, there are several barriers that must be overcome. First, vein, as compared to arterial, walls are thin, only a few cells thick at points, and the force used to maneuver the guide wire may result in puncturing both sides of the vein, thus wasting the catheter and destroying usefulness of the vein distal to the attempt site for catheterization. Next, a metal guide wire is typically used in arterial catheters. Such a guide wire used in a peripheral intravenous catheter may not be flexible enough to effectively maneuver within a vein. It may also puncture a blood vessel wall, particularly veins. Finally, difficulties arise in administering any intravenous catheter or guide wire due to failure to easily locate the veins due to their flexible structure. As veins move in response to pressure exerted near them, multiple attempts to properly insert the catheter may be necessary, which in turn provides further pain and discomfort to the patient. Because of these barriers, few devices have successfully been able to cannulate thin and winding veins as well as such arteries. Analogous issues can exist in other catheterizations or placement of cannula or sheaths. A few examples are central venous catheters, arterial sheaths, and venous cord introducer sheaths.

Ultrasound or other supplemental tools or equipment are sometimes used with a separately handled puncture needle for catheterization. This requires a specific skill set and the overhead and added complexity of such sometimes costly equipment.

As is well known in the art, tens and even hundreds of millions of catheters are placed per year. Sometimes multiple sticks of the placement needle are required to get proper placement. It is particularly difficult with infants, children, the obese, or the ill. It is not simply a matter many times of slight positioning. It can result in blown veins or arteries. Therefore, the sheer numbers and failed attempts can result in expenditure of resources such as discarding incorrectly placed catheters as well as health professional's time. There is room for improvement in this technical field.

SUMMARY OF THE INVENTION

It is therefore a primary objective, feature, advantage, or aspect of the present invention to improve over or solve problems and deficiencies in the present state of the art. Other objects, features, aspects, and advantages of the invention are an apparatus and method which include one or more of:

a. promotes improved sub-dermal placement of the catheter or the like;
b. deters misplacement, puncturing, or other damage to blood vessels including peripheral veins and arteries;
c. can be facilitated at least in some forms by one hand operation;
d. is noncomplex;
e. is economical;
f. can be made portable, even hand-sized;
g. reduces wasted catheters and related instrumentation;
h. can save user time including presents a low-learning curve for its use;
i. lowers the probability of punctured through the desired location particularly in peripheral blood vessels;
j. avoids mistakes and sudden forceful movements at the sub-dermal location;
k. does not require other tools or equipment;
l. decreases likelihood of repeated vein punctures to patient and associated pain.

In one aspect of the invention, an apparatus comprises a hollow needle for penetrating skin and placement of its distal end in an intended internal position in a patient, including but not limited to a peripheral blood vessel. A hollow stabilizing component is slideable along the needle (inside or outside) from a retracted position to an extended position past the distal end of the needle.

The benefit of such an arrangement is that instead of simply subcutaneous puncturing to gain access to inside a patient (human or animal), and then either trying to deploy a catheter sheath or something similar or using simply a guide wire through the needle lumen and extend it out to assist, a tubular stabilizing member can be extended from the distal end of the puncture needle. That tubular member can serve as a catheter sheath guide. It can also accommodate a subsequent member sliding out along and out its hollow interior. This can provide a number of different possible functional benefits.

In one example, the secondary member is a stabilizing member such as a second hollow stabilizing component or tube of slightly smaller diameter than the first hollow stabilizing component. There could be further extensions from that combination.

In another example, the secondary stabilizing component could be what will be called a guiding element or guide wire. Instead of being hollow, it can be wire shaped. In one example, instead of more conventional metal guide wires such as might be used with the Seldinger technique, the guide wire could be plastic. It could be more flexible and less likely to puncture a blood vessel than a metal guide wire.

In a further example, a guiding element or wire is slideable through the hollow stabilizing component from a retracted position to an extended position past the distal end of the hollow stabilizing component.

Another aspect of the invention involves an actuator or mechanism proximal to stabilizer and guide wire components to control their step-wise deployment. In use, in a home position the stabilizer component and guide element are retracted. The distal end of the needle penetrates the skin to an intended internal position. The actuator allows the user to deploy at least the hollow stabilizer tube to its extended position. The actuator then allows the user to deploy the guide element to an extended position past the distal end of the extended hollow stabilizing component as a second step. This promotes proper placement of the extended guide element and deters misplacement or damage to internal tissues or vessels. Subsequently a catheter sheath or the like can be slid over and past the distal end of the needle, over the extended portion of the hollow stabilizing component and then over the extended portion of the guide element in its extended portion past the extended distal end of the stabilizing component, again promoting proper placement and deterring damage. The actuator allows retraction in a reverse manner. It can be in a two-step process.

The actuator or deployment mechanism does not have to be integrated with any housing or body associated with the needle, hollow stabilizing component, or a further stabilizing component. On the other hand, it can be integrated. In that aspect, the entire system can be integrated in basically one tool or instrument. For intravascular catheterization, it can be hand held size and even operable one-handed.

In another aspect of the invention, the hollow stabilizing component is essentially sized for coaxial sliding within the lumen of the needle. The guiding element is sized for coaxial sliding within the lumen of the hollow stabilizing member. Thus, the slightly larger diameter needle can penetrate the skin, the hollow stabilizing member and guide element can be stored in retracted position in the lumen of the needle. The two step deployment of the stabilizing component and then the guiding element can occur. In one aspect, the outer diameter of the stabilizing component is slightly less than the inside diameter of the lumen of the needle in which it slides. This can allow blood or fluid entering the distal end of the needle to flow between the exterior of the stabilizing component and lumen of the needle. This can allow, as an optional feature, backflow of blood or fluid into a flash chamber that can give the user a visual indication of whether the needle has been placed in a desired position. An example would be a backflow of blood from a blood vessel to give the user high assurance of proper placement in the blood vessel.

In another aspect of the invention, the actuator comprises a handheld body or handle, a cavity longitudinal through at least a portion of the handle, a manually manipulatable control for deployment of the stabilizer component from retracted to extended position and vice versa, and a manually operated control for independent actuation of the guide wire or element from a retracted to a fully extended position and vice versa. In one example, the actuating controls are slide elements. A guide in the actuator body or handle allows slideable movement of both controls for a first stage deployment. Both the hollow stabilizing component and guiding element could be moved from fully retracted positions proximal to the distal end of the needle to a first extended position extended from the distal end of the needle.

An example of the guide would be a slot arrangement or system in the body/handle. In one example, the controls and guiding structure in the actuator handle comprise essentially a key and slot arrangement. The first step deployment allows a single pushing forward of sliders (keys) along a first slot basically aligned with the longitudinal axis of the needle. A transitional slot transverse to that first slot would allow a second slider to be moved to a second spaced apart but parallel slot that extends farther distally to allow the second step deployment of just the guiding element. The slot arrangement can allow the actuating body or handle to be held in one hand, and a thumb or finger of the user control both steps with that one hand with high assurance of the correct order of deployment. It can also give tactile feedback regarding whether each or any of the components being introduced through the skin is deemed to be moving to the desired location inside the patient's body.

Another aspect of the invention comprises an apparatus, including in any of the forms described above, further including a catheter sheath that can be installed over the needle prior to introduction of the needle into the patient. It can be separated from the apparatus once high assurance of desired placement of the deployed needle, hollow stabilizing component, and guiding element are confirmed.

In another aspect of the invention, the apparatus and catheter combination described above are further combined with a connection between the catheter and either a supply of fluid or a container for receiving fluid from the location of the distal end of the catheter in the patient's body. The apparatus deploying the needle, stabilizing component, and guiding element would be removed once the catheter sheath is in place in the patient. The catheter sheath would have a connection to tubing or the like. That tubing can be connected in fluid communication with other components. Examples of the same would be a container to receive blood from a blood vessel for further use. Another example would be a supply of intravenous fluids, including pharmaceuticals, to the patient.

These and other objects, features, aspects, and advantages of the present invention will become more apparent with reference to the accompanying specification and claims.

BRIEF DESCRIPTION OF THE DRAWINGS

FIGS. 1C, 1D, and 1E are enlarged exploded views of certain components of FIG. 1B.

FIGS. 3B, 3C, and 3D are plan views from different perspectives of the apparatus of FIG. 3A in its first position (all extendable components retracted).

FIG. 3E is a sectional view taken along line 3E-3E of FIG. 3D.

FIGS. 3F and 3G are back and front elevation views respectfully of FIG. 3C.

FIGS. 3I-M are enlarged isolated views of portions of FIG. 3E.

FIGS. 4A-4H are identical to FIGS. 3A-3H except the apparatus is in a second position namely where manually actuatable sliders move the coaxial hollow stabilizing component and guide wire from home or fully retracted positions to extended positions past the distal end of the needle along the vein.

FIGS. 5A-5H are identical to FIGS. 4A-4H except the device is in a third position where the dedicated slider controlling the guide wire is manipulated to its dedicated separate slot and moved to fully extend the guide wire past the extended position of the hollow stabilizing member along the vein.

FIG. 8C shows a first step deployment of a hollow stabilizing component from the distal end of the needle.

FIG. 8D shows a second step deployment of a guide wire from the hollow stabilizing component.

DETAILED DESCRIPTION OF EXEMPLARY EMBODIMENTS OF THE INVENTION

Overview

Figure 1A:
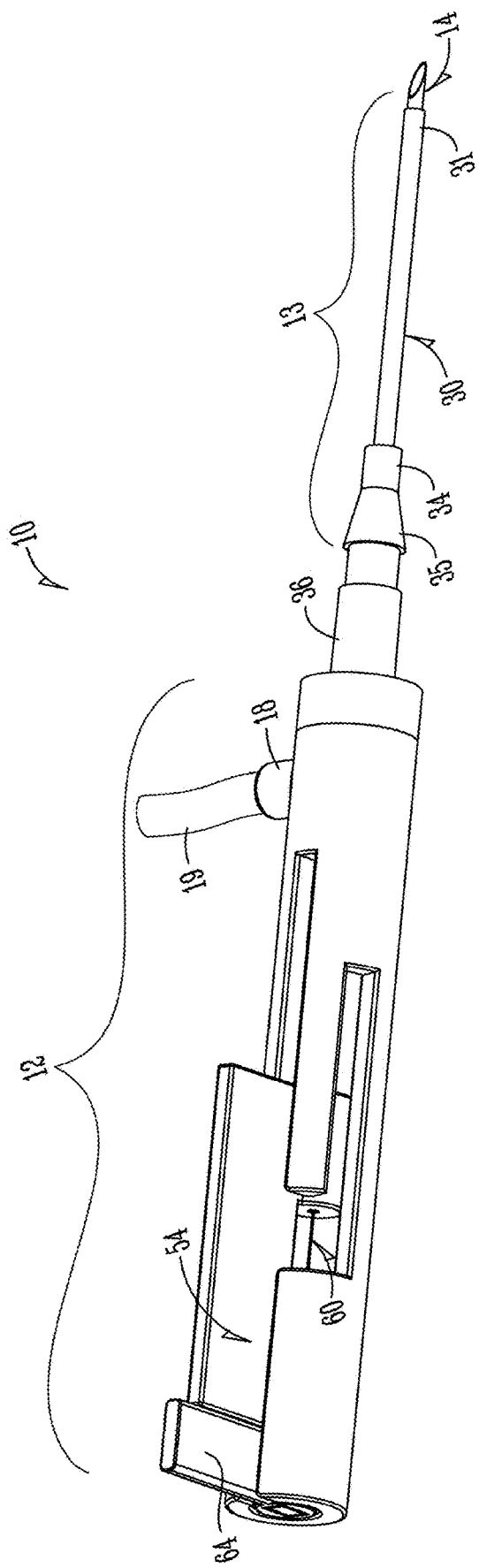
FIG. 1A is a perspective view of an assembled version of a first exemplary embodiment according to the present invention.

For a better understanding of the invention, below is a description in more detail of examples of several forms the invention can take. It is to be understood these are neither inclusive nor exclusive of all such possible forms and configurations.

Frequent reference will be made to the appended drawings. Reference numerals will be used to refer to certain parts and locations within the drawings. The same reference numbers apply to all the drawings unless otherwise indicated.

These exemplary embodiments will be described primarily in the context of use with peripheral venous catheterization. It is to be understood, however, that it can be applied in any context in analogous ways. In other words, it is not limited to peripheral venous catheterization. Examples of other possible uses include but are not limited to any other catheterization of analogous uses. As is appreciated by those in this technical field, intravascular catheterization is but one species of catheterization.

Exemplary Embodiment One

With primary reference to FIGS. 1-7 and any sub-parts, an apparatus according to a first exemplary embodi-ment can include a hand held body or handle 12, and sliders or slideable controls 54 and 64 that slide within a slot arrangement in handle 12.

Figure 1B:
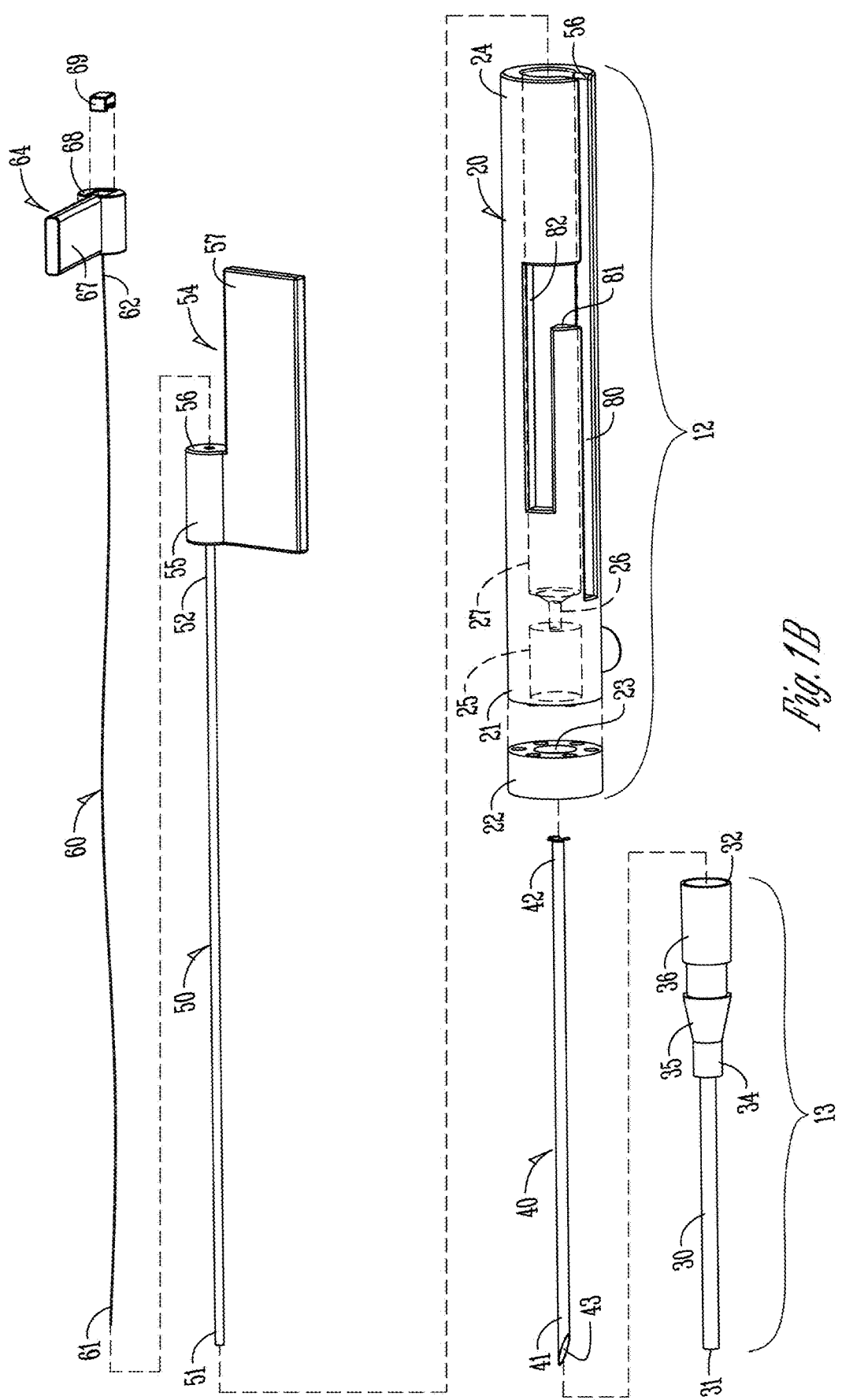
FIG. 1B is an exploded view of FIG. 1A.

A coaxial combination of needle 14, what is called a hollow stabilizing component or HSC 50, and a flexible thin guide element or wire 60 are operatively mounted relative to handle or body 12 along a longitudinal axis (see FIG. 1B). As shown in FIG. 1A, a catheter sheath and hub 13 are slid over and backward or proximally from the distal end of needle sub-assembly 14 prior to use of apparatus 10. Catheter subassembly 13 is thus left in place after apparatus 10 guides it into place and is removed.

In this embodiment, the length and diameter of handle sub assembly 12 is approximately three inches long by a half of an inch diameter. The slide controls 54 and 64 extend to different radial heights relative to body 12 as shown in FIG. 1A. The length of the slots in which slide controls 54 and 64 are coordinated such that, in retracted position, hollow stabilizing member 50 and guide wire 60 are fully retracted from the distal tip of needle 40 of needle sub-assembly 14 (when in fully retracted position). In this example, full extension of HSC (hollow stabilizing component) 50 and then guide wire 60 will be approximately equal to a length of the catheter assembly 13.

Catheter and Needle

Catheter assembly 13 and needle sub-assembly 14 can be conventional as would be appropriate for the given application for the apparatus. Both could be obtained commercially off the shelf. For example, needle sub-assembly 14 could be a metal, beveled distal end, hollow needle or trocar for peripheral venous catheterization. But it could be the type for other forms of catheterization. Typically this is 18-22 gauge as well as lesser used gauge sizes. Gauge size would be selected based on application (e.g. peripheral venous catheterization versus others) and based on diameter of the coaxial guide wire and coaxial hollow stabilizing component. Catheter tube, cannula, or sheath 30 would have an internal lumen diameter that would closely fit over the exterior of needle sub-assembly 14 but be slideable inside it. Thus, hollow stabilizing component 50 would have a slightly smaller outside diameter than the inside diameter of the aluminum needle sub-assembly 14 and be slideable therein (including in this example having space allowing blood to flow therebetween). The distal end 31 of catheter sheath 30 could be blunted (e.g. to avoid inadvertent vessel puncture). These catheter sheaths are typically quite thin and have a degree of flexibility.

Once the device of FIG. 1A is in place, catheter sub assembly 13 can be slid forward on needle sub-assembly 14, HSC 50 and/or guide wire 60 can be extended, and then everything removed to leave just catheter sub assembly 13 in place. Normal utilization of that properly placed catheter can proceed such as is well-known in the art. One example is diagrammatically shown in FIG. 2. Further description of use of catheter 13 will not be set forth.

Handle

FIGS. 1B and 1C illustrate construction and com-ponents of each subassembly. Handle or body 20 can be made out of a number of different materials. Moldable plastic is one. Others are possible. A cavity extends between distal open end 21 to proximal open end 24. As illustrated in FIG. 1B, a flash chamber 25 is succeeded by constriction 26 which is suc-ceeded by a proximal chamber 27 between those open ends. A cap 22 with through bore 23 holds in place proximal end 42 of needle 40 of needle sub-assembly 14 and mounts to distal end 21 of body 20. It can be connected by adhesive, fasteners (such as screws), or other techniques.

Flash chamber 25 is optional but can provide a collection space for blood flowing back from a pierced blood vessel. A side port 18 has an opening 29 in fluid communica-tion with flash chamber 25. A transparent or partially trans-parent container 19 could be pre-connected to side port 18 and collect spill-over blood out of flash chamber 25. This can provide a visual indicator to the user that the needle has accessed a blood vessel. One example of such a flash connec-tion 19 to side port 18 would be a piece of trans-parent plastic surgical grade tubing with its distal end closed off. Option-ally, that distal end could be bent over and glued to the side of body 20 to provide a U-shape visual "flash chamber". As will be appreciated by those skilled in the art, flash chamber 25 is in the interior end handle 20. There could be a window or a light transmissive (transparent or translucent) section of handle 20 that would allow the user to visually see blood filling into chamber 25. In such situations a side port and added flash vessel outside handle 20 may not be needed.

However, to the extent side port 18 is utilized, the vessel container for visually seeing a flash of blood that flows through flash chamber 25 and outside port 18 could be such things as a short section of light transmissive surgical tubing or the like, some sort of light transmissive container or bag, or something similar. Furthermore, it could either be a closed volume of space (like a closed end length of tube) or it could have a limited liquid space but either have an air vent or a valve that could release air or blood from that space. There are many ways in which the user could visually identify a flash of blood coming back. A further potential example would be some sort of bracket along handle 20 that would attach a short length of tubing or other visually perceivable container space for a flash chamber outside the handle body. Additionally, a side port 18 could simply connect to a collection container or some other system for either collecting fluid from the subcutaneous site of the needle or possibly infuse fluid from a source outside of handle 20 through side port 18 and down needle 40 and out its distal end 41.

Handle body 20 not only is configured to have a space between the outside diameter of the HSC 15 and the inner diameter of needle 40 (to allow blood to backflow into flash chamber 25), but also needle body 40 is fixed to cap 22, which is in turn fixed over flash chamber 25 of handle body 20.

Figure 3A:
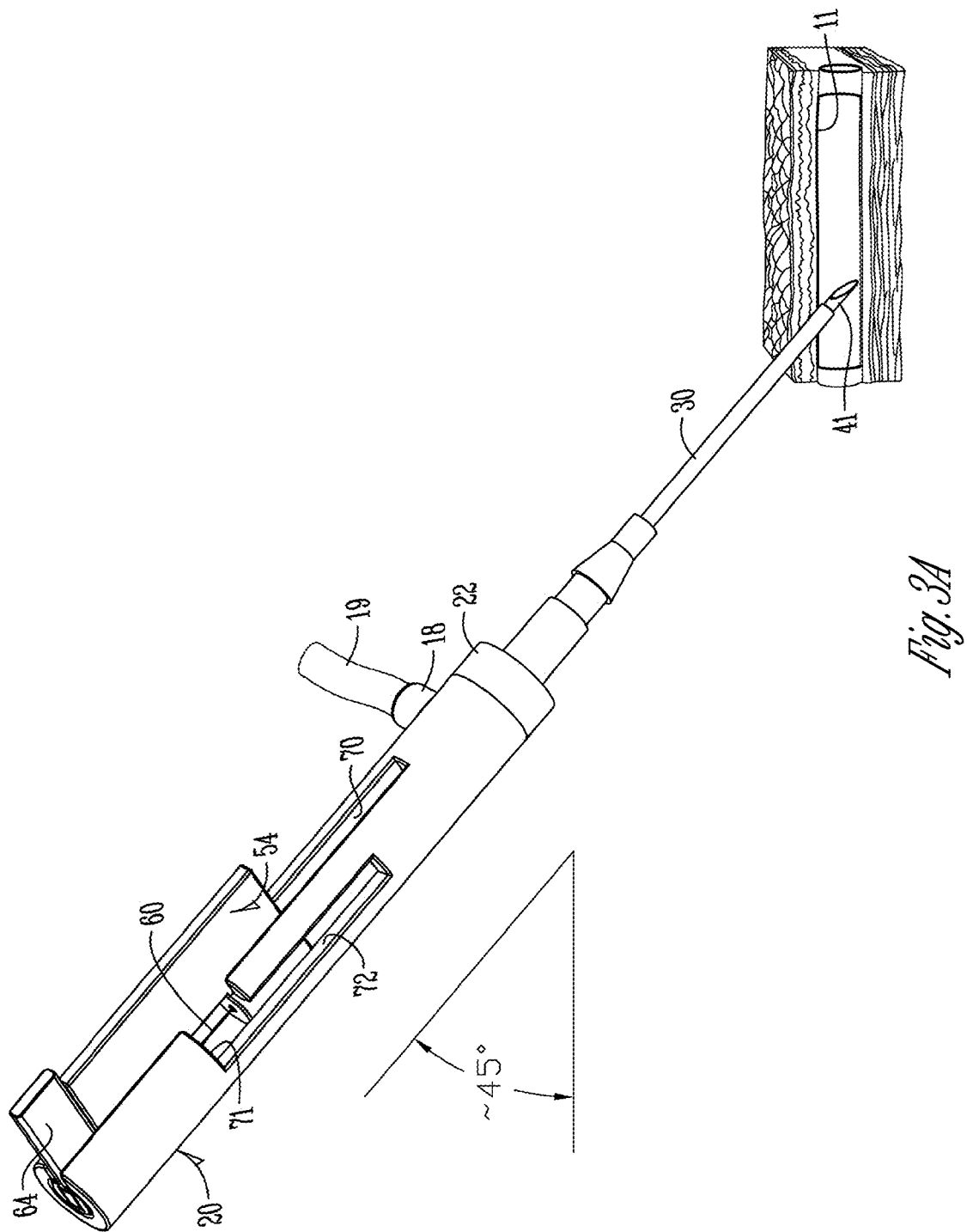
FIG. 3A is similar to FIG. 1A but shows the apparatus in a first position (stabilizing component and guide wire in home or fully retracted positions) with the needle in place in a peripheral vein.
Figure 3H:
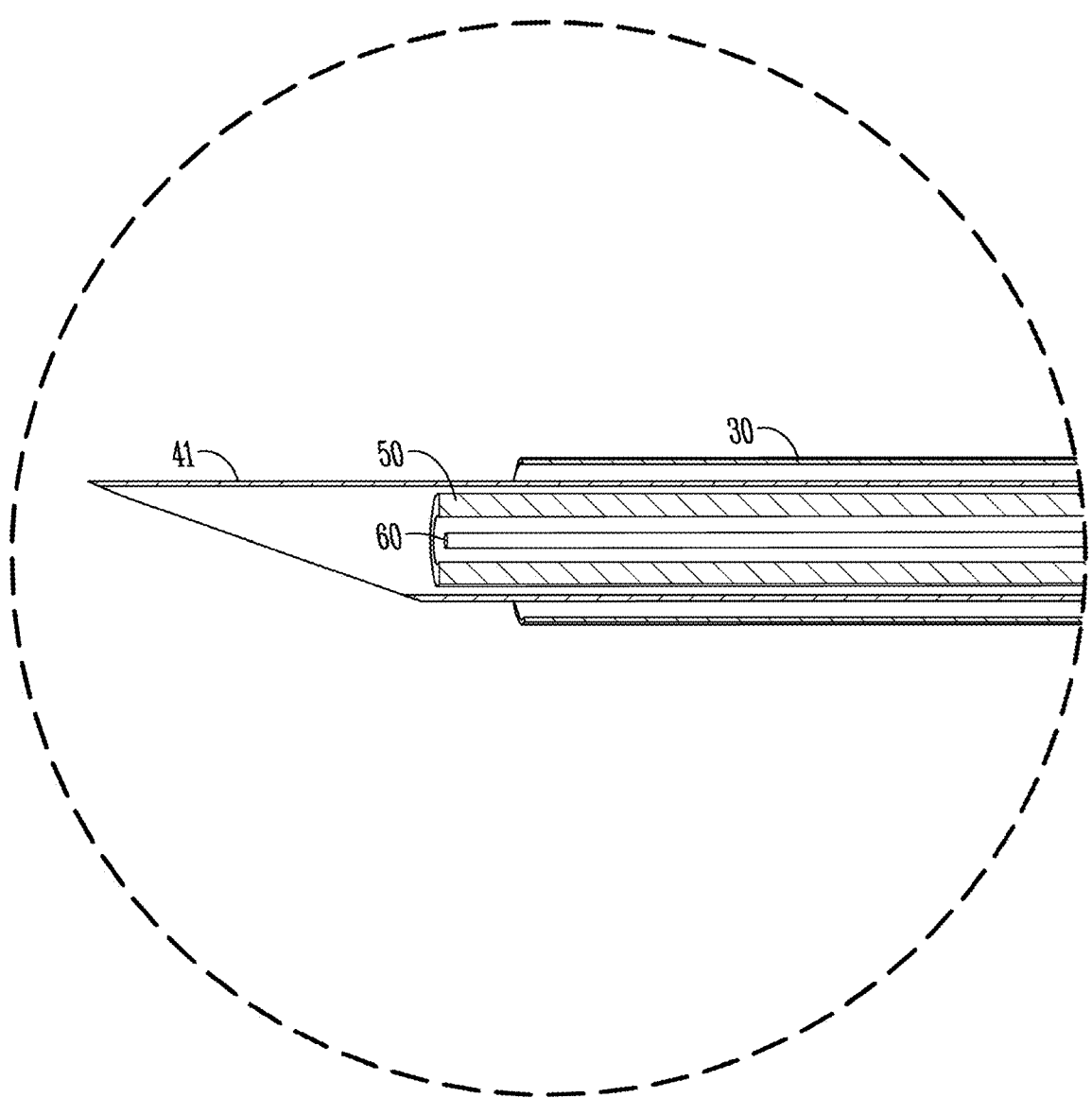
FIG. 3H is an enlarged isolated view taken along line 3H of FIG. 3E.
Figure 31:
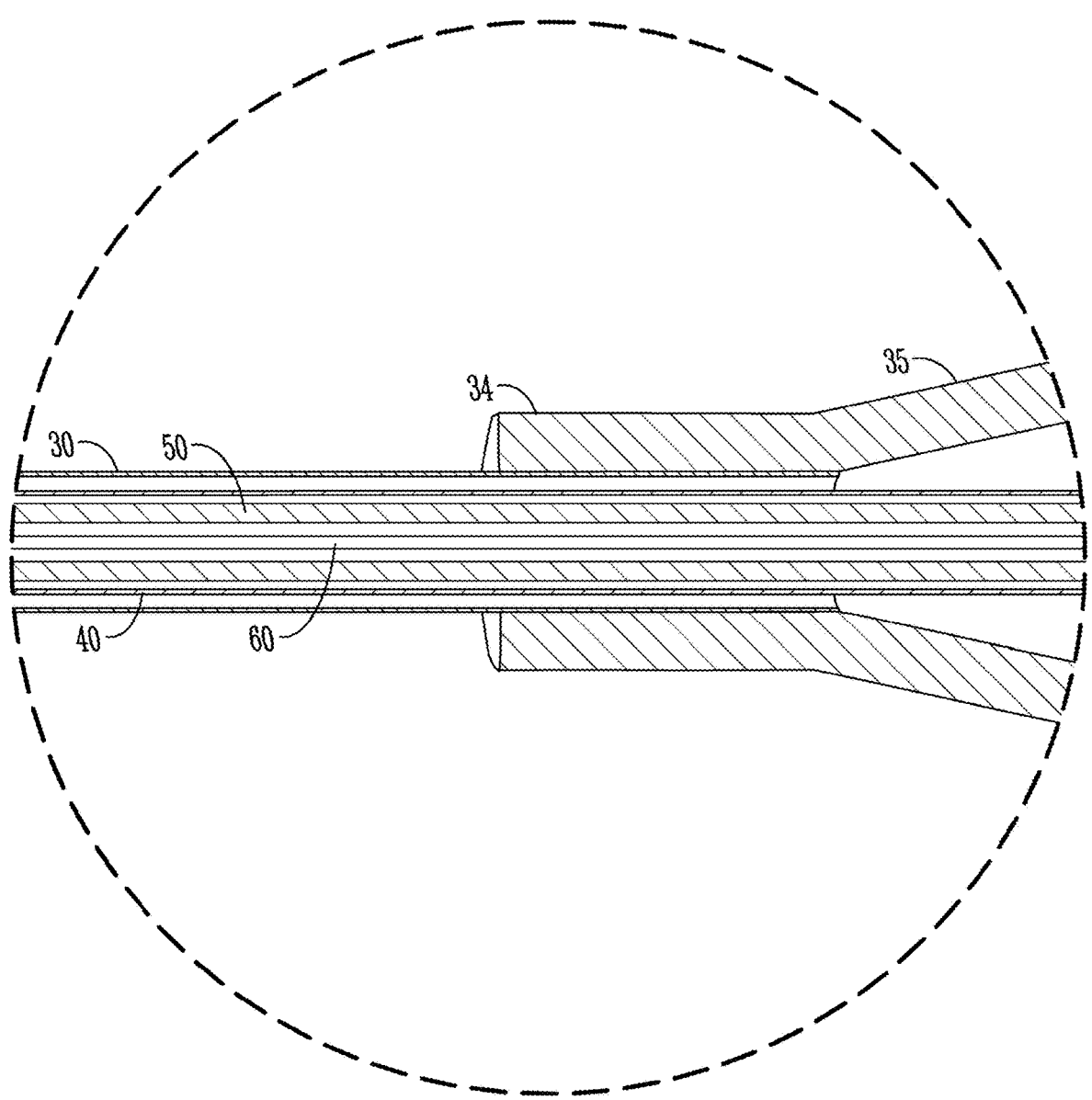
Figure 3J:
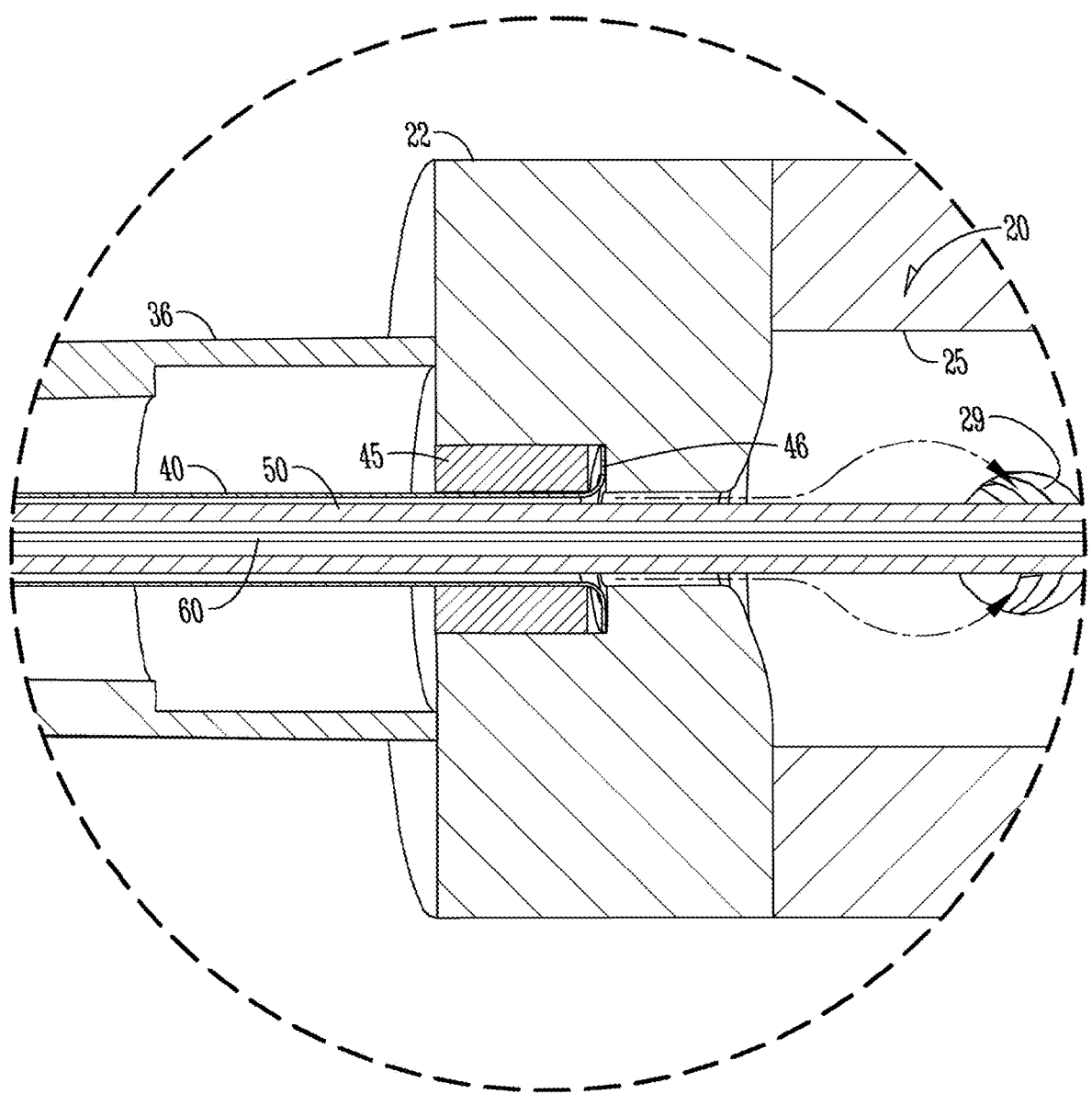

As shown in FIG. 3J, proximal end of needle 40 should be secured or fixed to a counter-sunk partial bore by having a flared proximal end 46 that would then be secured in place by an interference fit or adhesively connected plug 45. Other ways of securement to cap 22 are possible. This arrangement would seal or be a barrier from blood moving back between the exterior needle 40 and the passageway through cap 22.

The short section (e.g. one inch of clear plastic surgical tubing 19) could receive blood through the passageway of opening 29 and allow visual confirmation of placement of distal end of needle 40 in a blood vessel. If the "flash" of blood stops or slows, the user can back up the distal end of the needle or withdraw it and reposition it until confirmation is made. Tube 19 can have a closed distal end. Because of size, makeup of components, and materials, the entire assembly 10 can be made economically and thus be dispos-able.

The shape, size, and function of handle subassembly 12 includes being able to operate apparatus 10 by holding handle body 20 in one hand. Sliders 15 and 16 are opera-tively mounted in handle body 12 as well as operatively connected to HSC tube 50 and guide wire 60 which are coaxially positioned along the longitudinal axis of needle 40. What would be called a lock and key system includes a slot arrangement formed in handle body 20. Two longitudi-nal slots are coordi-nated with HSC tube 50 and guide wire 60 for a two-step deployment. The operator can push on slider 64 which would move slider 54 concurrently until slider 54 reaches the distal end of first slot 70. This is the first step deployment of HSC tube 50 beyond the distal end of needle 30. A transitional slot 71 allows the user to transition slider 64 to the second slot 72 in handle 20. By correlation of the length of slider 54 versus slider 64 longitudinally, and the point of attachment in length of both HSC tube 50 and guide wire 60 to those slider plates 57 and 67 of sliders 54 and 64 determines how far the distal ends of HSC tube 50 and guide wire 60 can be extended relative the distal end of needle 30. Furthermore, the slot system 70, 71, and 72 ensures that the correct order of deployment occurs. The slots also guide the user in operation which can be by grasping handle body 20 underneath and wrapping four fingers around it with needle 40 extending outwardly between the first finger and the thumb and then using the thumb to slide slider plates 57 and 67. This can be done in either direction for two-step deployment outwardly and two-step retraction. Slide controls 54 and 64 can be made of different materials including plastics similar to body 20.

Materials for handle or body 20 and other components can be of a variety of types. One example would be any biocompatible or surgical grade plastic that could be formed in a manner needed or desired. Its properties would have sufficient durability and rigidity for the described purposes.

Needle

Needle subassembly 14 (FIG. 1C) can include a standard catheterization metal needle 40 with sharp beveled edge 41 and open proximal end 42. As indicated in FIG. 1B, catheter subassembly 13 could be slid over needle 40. Catheter subassembly 13 can include what might be called a hub 36 including a luer, threaded, or other connection for connec-tion to another tube to some type of collection or infusion system 17 (see FIG. 2). This is conventional in the art. A transitional section and conical nose 35 would receive the proximal end of catheter sheath 30 and hold it in position. The sheath distal end 30 would fit over needle body 40 to almost the beveled end 41 when in beginning or home position. It would be available then to slide forwardly on needle body 40 into final interior position in a user's blood vessel while leaving hub 36 exterior above the hand to connect up to the system 17 of FIG. 2 as appropriate.

Hollow Stabilizer Component (HSC)

Hollow stabilizer component ("HSC") subassembly 50 (FIG. 1D) would include a flexible tube having opposite open distal and proximal ends 51 and 52. The tube of HSC 50 would fit into and be secured within a through-bore 66 in a carriage portion 55 of slide control 54. A plate or slider portion 57 extends from sliding carriage 55 and is available for the user to manually move.

The tube of HSC 50 can be secured or fixed into throughbore 56 by any number of techniques. One would be adhesive. Another would be interference-fit. There could also be an enlarged chamber around through-bore 56 that could allow injection of adhesive or installation of some sort of retention member.

In this embodiment, some characteristics of the tube of HSC 50 are as follows. Its length is approximately half the length of cannula 36 of the catheter subassembly 13. Its lumen diameter is slightly bigger than the outside diameter of needle body 40. It is made of a plastic material that has some degree of flexibility yet has sufficient rigidity to be pushed by slide control 54 from its proximal end through needle body 40, out distal end 41 of needle body 40 and, for example, into the lumen of a blood vessel. It can experience some resistance to that movement and retain its general longitudinal shape, however, it can flex. This can help, for example, HSC 50 to bounce off or deflect instead of puncture, and/or otherwise follow the lumen of the blood vessel. The material has been selected for this embodiment to do so even for the relatively thin peripheral veins associated with peripheral venous catheterization. Some veins can be only a few cells thick. The material deters puncturing of even such thin walled vessels. An example of the material is polyurethane. The polyurethane tubing could be selected to have a degree of flexibility. For example, it could be more flexible than the rigid metal needle 40. By further example, it could be less flexible than plastic guide wire 60, including the exemplary commercially available fishing line mentioned previously. The designer can select the degree of flexibility based on the material properties of the polyurethane. In this exemplary embodiment, HSC 50 would have a degree of flexibility that is not as much as the plastic guide wire 60 but is sufficient to allow some flexure so that it promotes following a blood vessel once deployed out of properly placed needle. It would then add sufficient rigidity to both guide the guide wire 60 along its distal end and out into that blood vessel as well as later guide catheter sheath 30 over it. Other materials with analogous properties are possible.

As previously mentioned, the outer diameter of HSC tube 50 will be selected to be smaller than the internal diameter of needle 40 so that it can slide therein and allow blood to move backwards approximately to flash chamber 25. The length of HSC tube 50 is selected to be in retracted position just proximal of the distal tip of needle 40 (see FIG. 3H). And, as mentioned, the proximal end of HSC tube 50 would be fixed to slider 15. The material for HSC tube 50 in this embodiment is selected to have a degree of longitudinal rigidity but a degree of flexibility such that when it exits needle 40 it can deflect relatively easily, including thin walled peripheral veins. On the other hand, it provides a degree of stiffness or support over which catheter sheath 30 can be slid or manipulated.

In this embodiment HSC tube 50 is made of polyurethane. An example could be Dow Pellethane 2363, with a durometer 40-65 Shore D.

It should be understood, however, that variations to these material properties are possible. Additional material properties such as puncture resistance, chemical resistance, potential strength, color, and the like can be selected as according to need or desire. The material is biocompatible and meets all requirements for catheterization. It is strong enough to hold and guide the catheter sheath with a high enough modulus not to break.

Guide Wire

Guide wire 60 can be essentially a conventional guide wire used with Seldinger technique catheterization. Its length is from a proximal connection to slider 16 to essentially the same distal location and just proximal of the distal end of needle 40 when in home position (see FIGS. 3H and 3E). Guide wire 60 slides through the lumen of HSC tube 50.

Some of its functions are to provide structural support for the catheter cannula beyond the distal end of needle 40 for a portion of the way to its final intended position while having a degree of flexibility to bend to follow the blood vessel. Guide wire 60 in this example is made of a plastic monofilament. An example of the material is nylon or nylon based monofilament. One example is fused fishing line under the brand name Fireline Crystal from Berkley Fishing, Spirit Lake, Iowa (USA).

Its distal end 61 can be blunted or rounded to prevent inadvertent puncture of a vessel wall distal to the puncture needle. It proximal end is connected to disc 68 by adhesion, sonic welding, tying, or otherwise. When disc 68 is seated in the proximal end of carriage body 65 of slider 16 and plug 69 inserted over disc 68, this fixes guide wire 60 to slider 16 so that it can accept longitudinal force on guide wire 60 to deploy it. In this embodiment, the diameter of guide wire 60 fits within the lumen HSC tube 50 and slides therein. It has been selected to deter the risk of puncturing even the relatively thin blood vessels used for peripheral venous catheterization as well as have flexibility to follow the blood vessel once needle 40 appropriately penetrates it. Its length between distal and proximal ends 61 and 62 is selected so that it slides within lumen 53 of HSC 50 by pushing its distal end 62 with second slide control 64. It can be held in place inside 64 by threading it through bore 66 and adhering it with glue, tying it, or otherwise affixing it to disk 68 that would seat within a depression in the proximal end of slide 64. A plug member 69 can interference fit or be glued into that depression over disk 68 to further hold it in position.

Guide wire 60, sometimes referred to as guide element, can be made of other materials. Other plastics are possible. Metal is also possible. Distal end 61 can be rounded or blunted regardless of the material.

Assembly

Assembly of apparatus 10 can proceed as follows. The distal end 61 of guide wire 60 can be threaded into opening 56 in slider carriage 55 and then threaded through the lumen of HSC tube 50. The plates 57 and 67 of sliders 15 and 16 would be aligned in the same plane and then that whole combination inserted in proximal open end of handle body 20. The coaxial distal ends 51 and 61 of HSC tube 50 and guide wire 60 would move through internal proximal chamber 27 in handle 20, and then into constriction 26; which is right along longitudinal axis of handle 20. The smaller diameter of constriction 26 would guide the HSC/guide wire combination through flash chamber 25 and out the distal open end of handle body 20 right along its longitudinal axis.

Figure 3K:
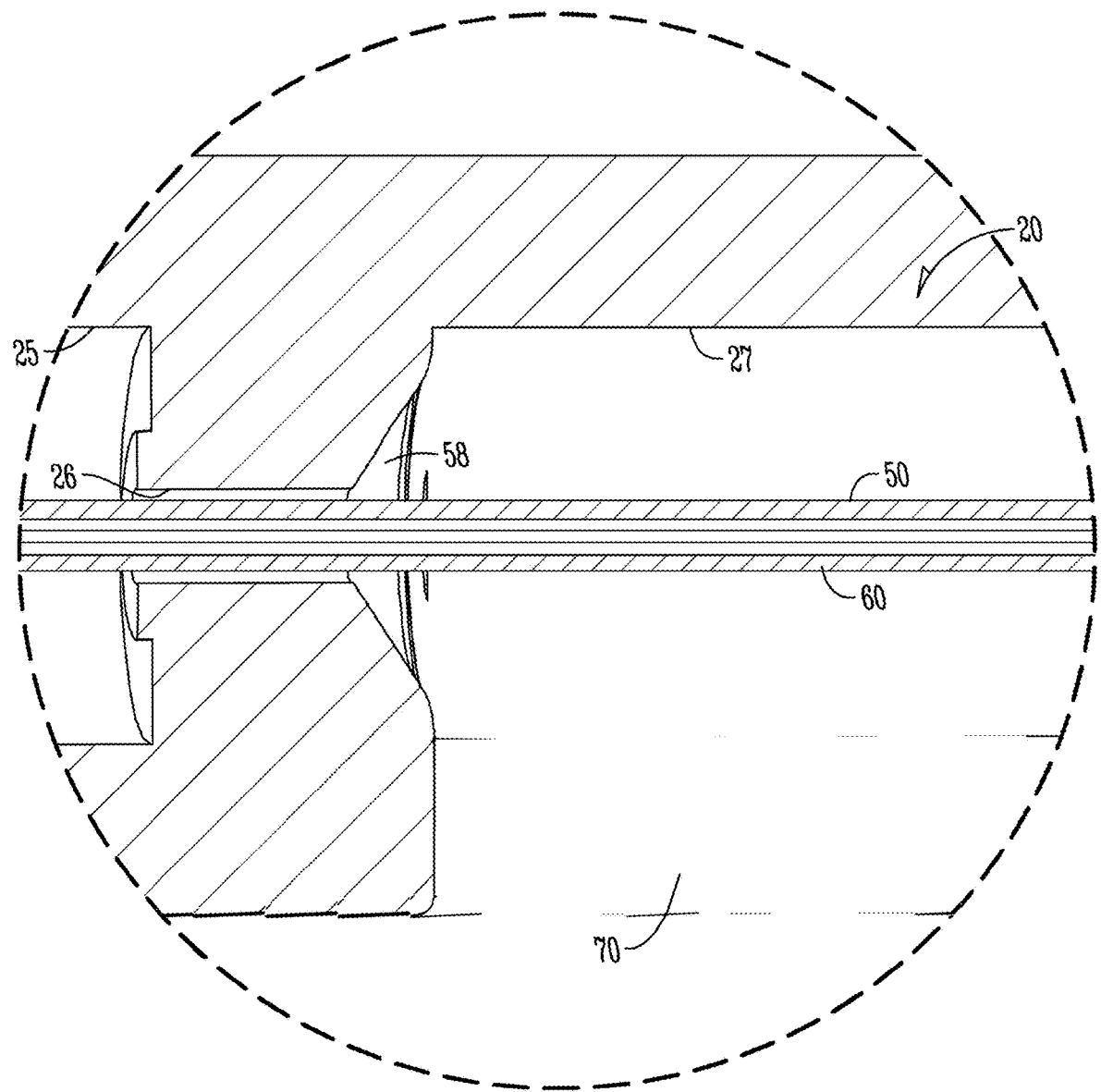
Figure 3L:
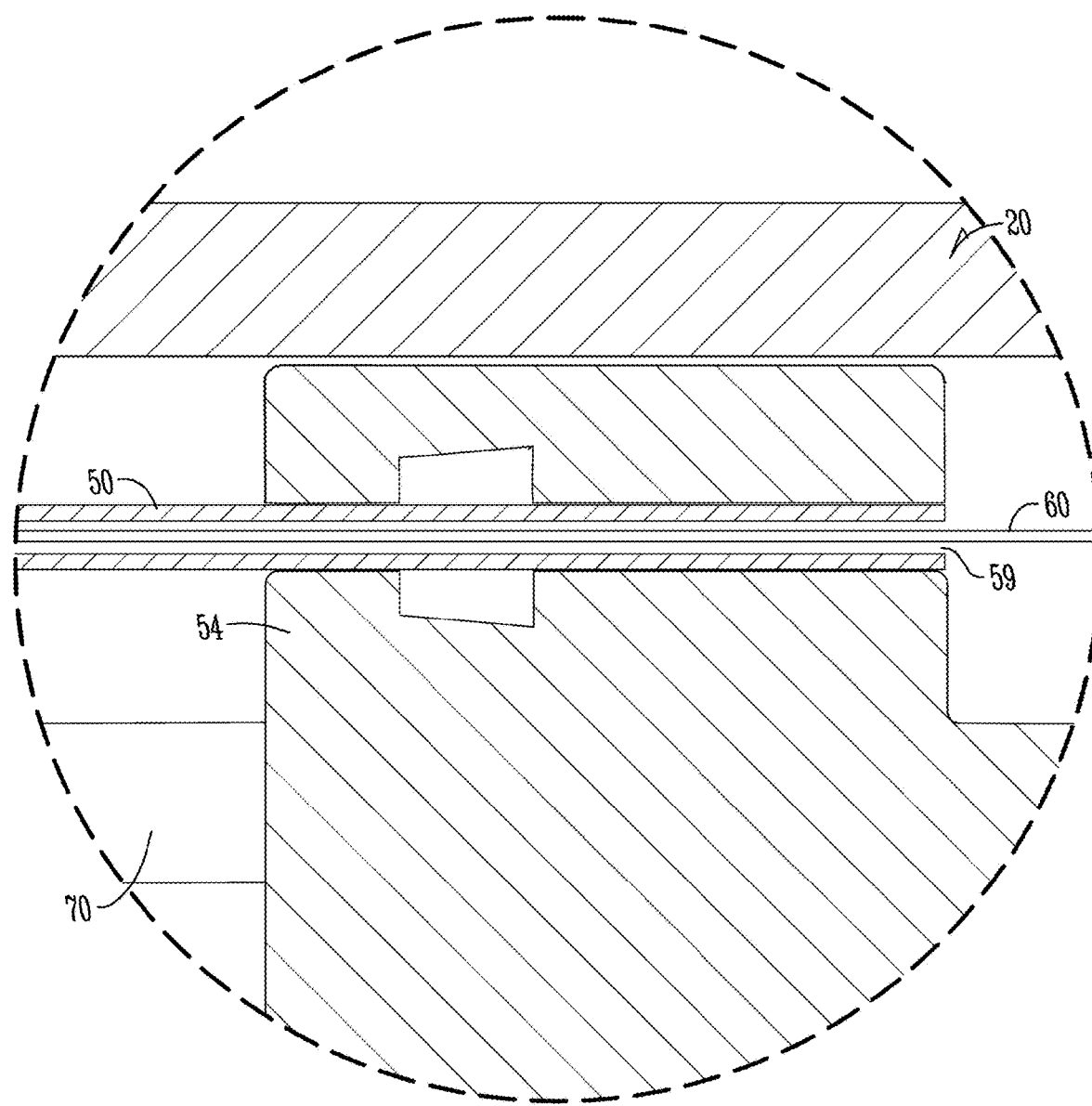
Figure 3M:
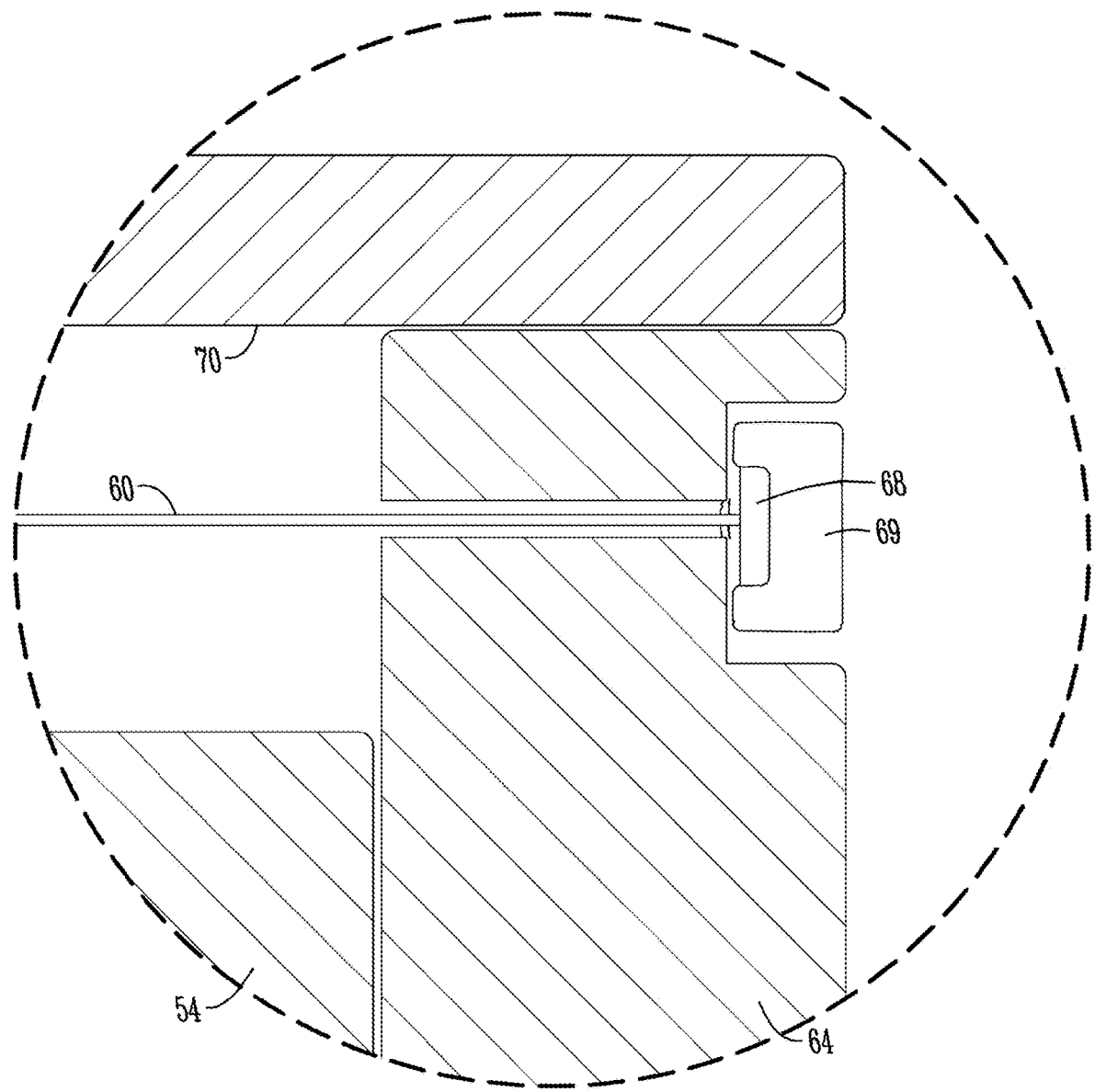

FIGS. 1C-1E illustrate an assembly of needle 40 to cap 22 (see also FIG. 3J), HSC tube 50 to slider 54 (see also FIG. 3L) and guide wire 60 to slider 64 (see also FIG. 3M), respectively. FIG. 1B then shows those subassemblies and their relationship to handle body 20. In both FIGS. 1B and 1 C, the commercially available catheter sheath 30/hub34/35/36 is shown to illustrate how it can be slid proximally on needle body 40 and essentially loaded for use on implement 10. As can be appreciated, the methods by which needle 40 is attached to cap 22 in a fixed relation, and likewise for HSC tube 50 to slider 54 and wire 60 to slider 64 can vary. As illustrated in FIGS. 3J, 3L and 3M, handle 20 can be created to have recesses, voids, slots, or other features that would facilitate such connections. For a few examples, a countersink bore in cap 22 could receive a plug 45 for a flared proximal end 46 of needle 40 to hold it in place in cap 22. As indicated at FIG. 3 L, a void or other slot could allow some sort of a locking member or injected adhesive to hold the proximal end of HSC tube 50 and slider 54. Configuration of holding the proximal end of guide wire 60 and slider 64 is indicated at FIG. 3M. Additionally, there could be barriers, seals, gaskets or the like installed along that longitudinal axis. For example, FIG. 3K shows a countersink 58 could exist in body 20 in which a gasket or seal could be placed to prevent fluid or blood from communicating in the chamber 27. A similar gasket could be placed over the proximal end of HSC tube 50 and around guide wire 60 (see the location of reference numeral 59 in FIG. 3L) to prevent blood or fluid from back flowing between guide wire 60 and the lumen of HSC 50 back and out of that proximal end of HSC 50. Other features could be integrated in instrument 10.

Needle 40 is fixed into cap 22 and held by adhesive, interference fit or other technique. That combination can then be brought up so that the center longitudinal bore 23 in cap 22 fits over the coaxial distal ends 51 and 61 of HSC tube 50 and guide wire 60 to align it with the lumen of needle 40. Cap 22 and affixed needle 40 can then be fastened to the distal end 21 of body 20. Plates 57 and 67 of sliders 15 and 16 would be aligned along main longitudinal slot 70 and pushed proximally until in position similar to FIG. 1A.

Catheter assembly 13 would be threaded onto the distal end 31 of needle body 40 and moved distally until hub 36 comes near or abuts cap 22. In that position (see FIG. 1A), distal end 41 of sheath 30 is just proximal of distal end 41 of needle 40. Essentially the catheter assembly 13 is loaded onto needle 40 before entering the patient. Flash tube 19 could be connected to side port 18 and, if desired, its closed end bent over and glued to the side of body 20.

As can be appreciated, by reverse movement, either slider 16 and its affixed guide wire 60 could be withdrawn from the whole assembly and/or slider 15 and HSC tube 50 by pushing sliders 15 and/or 16 out the back or proximal end of slot 70.

In this example, the relative dimensions of the handle, needle, HSC, and guide wire, compared to that of the catheter, are predesigned as follows. In home or fully retracted position for HSC tube 50 and guide wire 60, both are coaxial and proximal of the distal end 41 of needle 40. But when fully deployed, where slider 15 is slid to the extreme distal end of slot 70 and slider 16 is transitioned over and moved to the extreme distal position of slot 72, the combined distance of extension of HSC tube 50 and guide wire 60 will be approximately the same as the length of catheter sheath 30. Thus, when the catheter assembly is slid forward when apparatus 10 is deployed to fully extended state, distal end 31 of catheter sheath 30 would be at or near the extended distal end 61 of guide wire 60. Sheath 30 would follow over the extended portion of HSC tube 50 and then the extended portion of guide wire 60 to that position so that it has both support and guidance by those two stages after sheath 30 leaves needle 40.

In this example, the extension of HSC tube 50 from the distal end of the needle is approximately 0.660 inches. The extension of guide wire 60 past the distal end of the extended HSC tube is 0.739 inches. Cumulatively that is 1.454 inches. This would approximately match the length of the catheter sheath 30. The design of the connection points of the proximal ends of HSC 50 and guide wire 60 to their respective sliders 15 and 16, as well as the length of slots 70 and 72, would be coordinated to accomplish this result. While this precise arrangement is not necessarily required, in this example it is selected such that upon full deployment of guide wire 60 and HSC 50 (FIG. 5A), catheter sheath 30 need only then be slid a short distance forward to pass distal end of needle 40 and then the user would have both the extended section of HSC 50 and guide wire 60 to guide that sheath to a fully extended distal end of guide wire 60. This can guide and support that sheath to an intended location. It is to be under-stood that the Figures are not precisely to scale regarding the relationship of length of sheath 30 and fully extended lengths of HSC 50 and guide wire 60. But, the enlargement of FIG. 6 illustrates that principal.

Slots 70 and 72 are substantially parallel to the longitudinal axis of body 20 and needle 40. The connection of HSC tube 50 and guide wire 60 and the internal chambers in handle 50 are also along that longitudinal axis.

The configuration of sliders 15 and 16 relative to slots 70, 71 and 72 ensure there is no error in the order of deployment. The first step would be to combine sliding of slider plates 64 and 54 along slot 70 (starting from the home position of FIG. 3A once the distal end of needle 40 is deemed properly positioned in vein 11).

The distal end of slot 70 provides certainty to the user that HSC tube 50 is fully deployed to its extended position. At that point, the pre-designed geometry of sliders 15 and 16 does the following. The length of slider 54 aligns slider 64 with transition slot 71. The user simply pushes slider 64 sideways through transition slot 71 into slot 72. The length of slider 54 is too long to pass through transition slot 71 so it cannot be inadvertently or even intentionally moved out of slot 70. After slider 64 is moved to slot 72, slider plate 64 can be pushed forward to actuate the second step extension deployment—movement of guide wire 60 distally and out of HSC tube 50.

FIG. 1B indicates how the components are assembled and how the combination of slots 70, 71 and 72 are formed in handle 20. Slide controls 54 and 64 are guided by those slots as will be described further below.

Operation

Typically, apparatus 10 is placed in the user's palm with sliders 15 and 16 up or towards the user. Distal end 41 of needle 40, fixed in the end of handle 20, is then directed to a desired entry point at the patient's skin. It has been found that moving needle 40 forward into the skin at approximately a 45° angle can be beneficial. Once in that position, handle 20 can be dropped to a shallower entry angle (perhaps approximately 20°-30°) relative to the skin or to vein 11. The angle can be dropped if initial vein puncture is successful after visual confirmation in flash chamber/connector 25/19. This can be beneficial for subsequent deployment of HSC tube 50 and guide wire 60 via sliders 15 and 16.

By referring to FIGS. 3-8 and any subparts, operation of apparatus 10 of FIGS. 1A-1C can be further under-stood. In initial home position, slide controls 54 and 64 are pushed back proximally in handle body 20 (see FIG. 3A). Slide controls 54 and 64 can be serially moved beyond the proximal end body 20 individually or together which would remove the respectfully attached HSC 50 and guide wire 60 subassemblies if desired. But starting with the position shown in FIG. 3A, the user could visually direct distal needle end 41 towards a peripheral vein of a patient. As indicated in FIG. 3A, a typical angle of attack can be around 45 degrees although other angles are possible. By manipulation and experience, the goal would be for beveled needle tip 41 to penetrate the vein into the vein's lumen.

In this embodiment, the flash chamber option could help the user confirm proper needle placement. As indicated at FIG. 3H, a slight gap exists between the outside of HSC body 50 and the interior diameter of needle 40. Blood, under the patient's blood pressure, can flow in that space back into flash chamber 25. Opening 29 inside port 18 is in fluid communication. A visually transparent collection vessel (U-shaped closed end length of tubing) would allow the user to see a "flash" or small volume of blood would be indicative of the needle being properly placed in the peripheral vein.

FIGS. 3B-3M show various views of the assembly 10 in that first starting position. Other features are as follows. FIGS. 3H-3M show in enlarged fashion the general relationship between components include the gap between lumen of needle 40 and the outside diameter of HSC 50 all the way from distal end 41 of needle 40 in flash chamber 25. FIGS. 3B-3D, as well as FIGS. 3F and 3G show additional views of how sliders 54 and 64 relate to the other components when the device is in this fully retracted position.

The constriction 26 between flash chamber 25 and the proximal chamber 27 provides a stabilizing support for HSC tube 50 before it passes into and through the larger flash chamber 25. A similar size constriction in cap 22 does the same.

It should be noted that there can be some gap or space between guide wire 60 and the internal wall of the lumen of HSC tube 50 through which blood might move proximally and into handle 20. Some sort of 0-ring or other sealing technique might be utilized to prevent the same. However, since guide wire 60 must slide in HSC tube 50, it may be acceptable that the sizes of these two components might be so close that blood would not tend to travel all the way back in the handle 20.

Figure 4A:
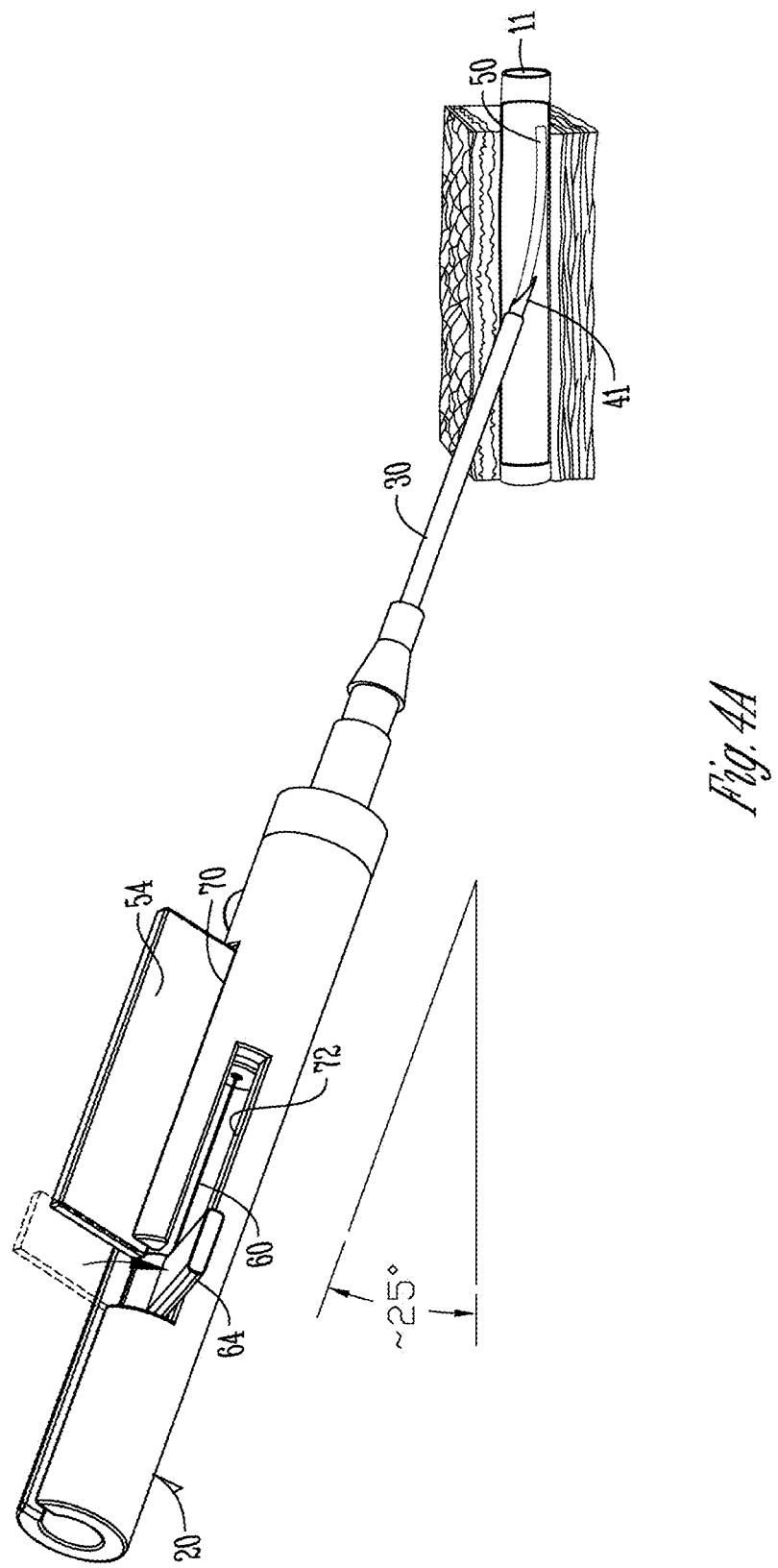
Figure 4B:
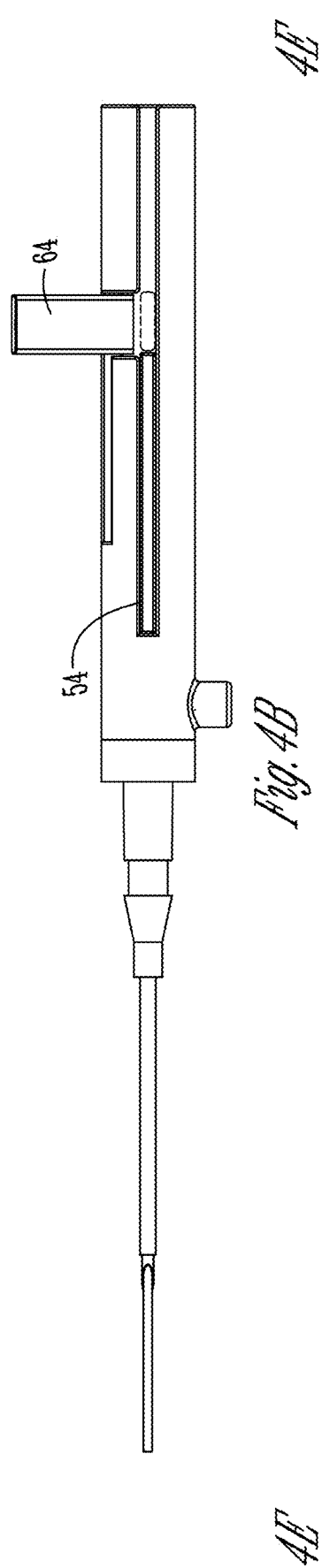
Figure 4C:
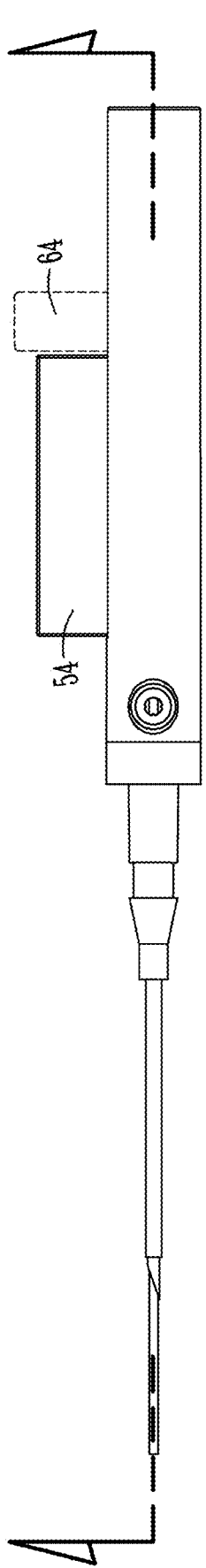
Figure 4D:
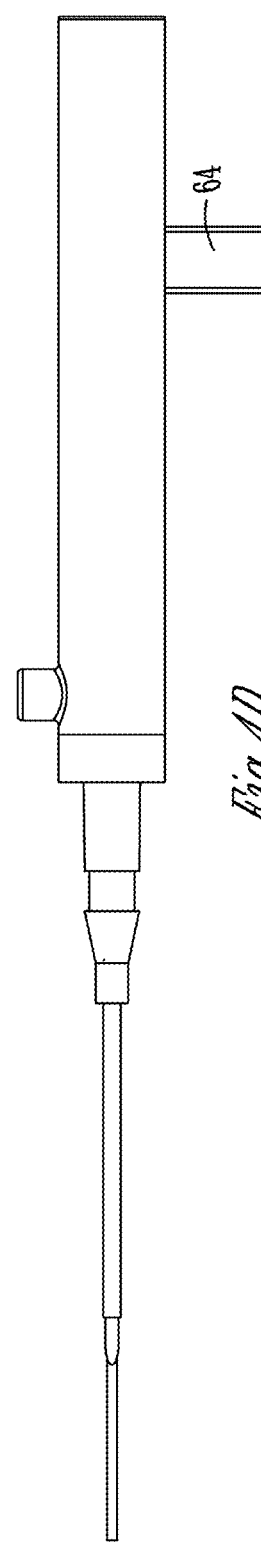
Figure 4E:
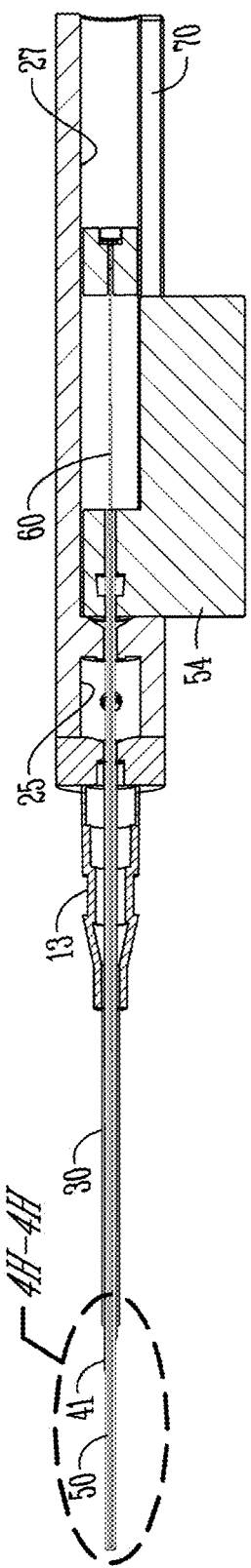
Figure 4G:
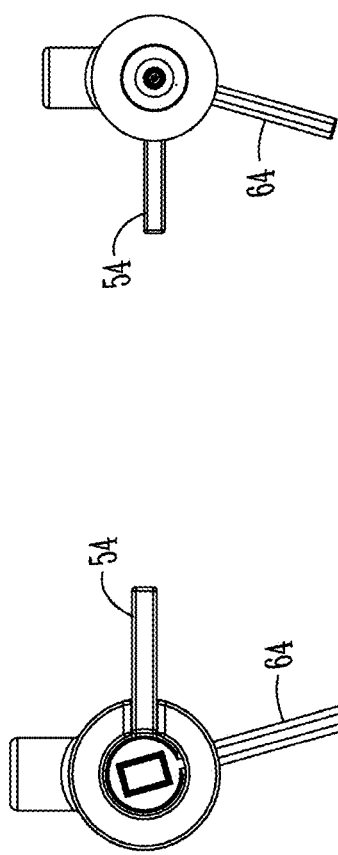
Figure 4H:
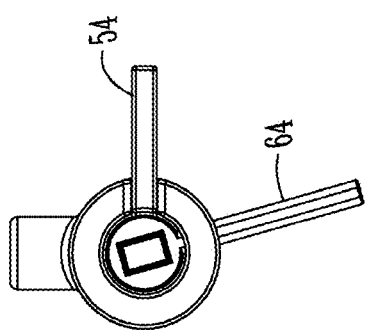
Figure 4H:
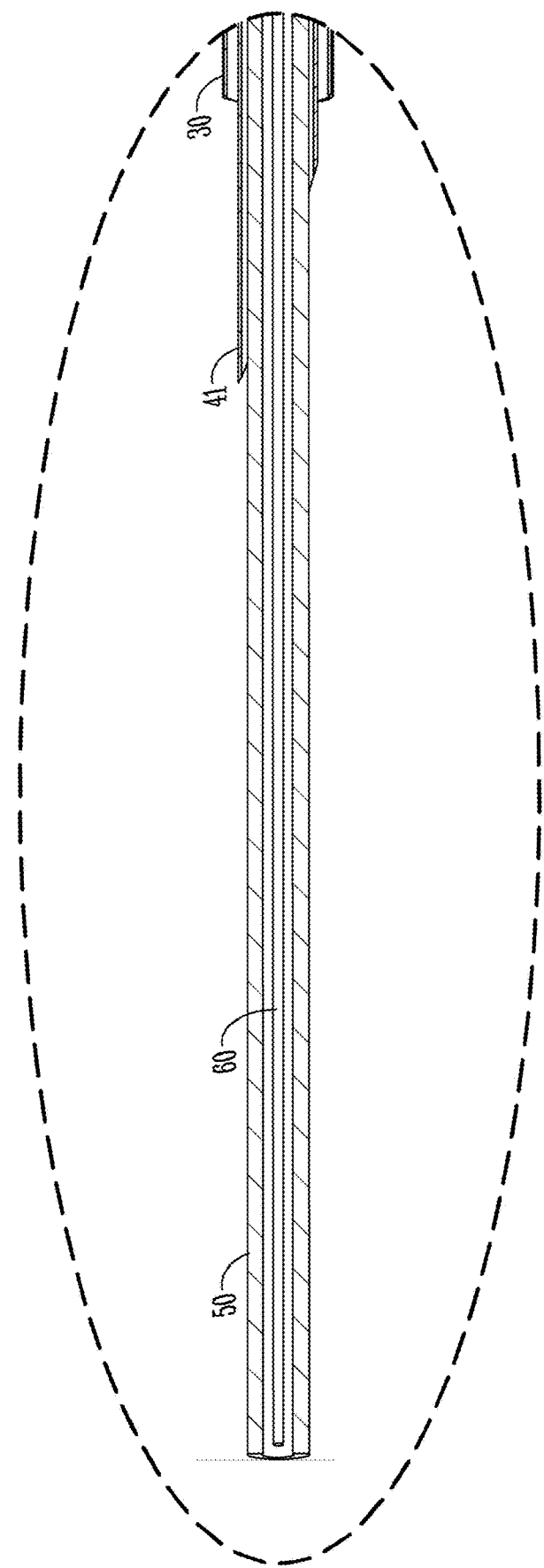

FIGS. 4A-4H show the intermediate position. Importantly, as shown in FIG. 4A, after the user pushes both slide controls 54 and 64 forward to where the distal end of slot 70 is a mechanical stop against further distal longitudinal movement, the narrower slide control 64 aligns with transition slot 71 (see ghost lines for slide 64 in FIG. 4A). This movement extends HSC tube 50 further into the blood vessel from the needle tip to provide a first length of guide and support for catheter cannula 30. The flexibility of tube 50 exiting from rigid needle 40 allows it to deflect or tend to follow the lumen of the blood vessel. In this position with a thumb or single finger, the operator can simply move a slide control 64 through transition slot 71 into second longitudinal slot 72 (see solid lines for slider 64 in FIG. 4A). The user should be able to feel resistance when advancing HSC 50 and guide wire 60. If resistance is felt, either can be retracted and needle angle adjusted for another attempt at deployment of either or both. FIG. 4B-4H illustrate position of sliders 54 and 56 from different viewpoints relative this first step of deployment. Cross section FIG. 4E and enlargement FIG. 4H give more details regarding the interior relationships.

Figure 5A:
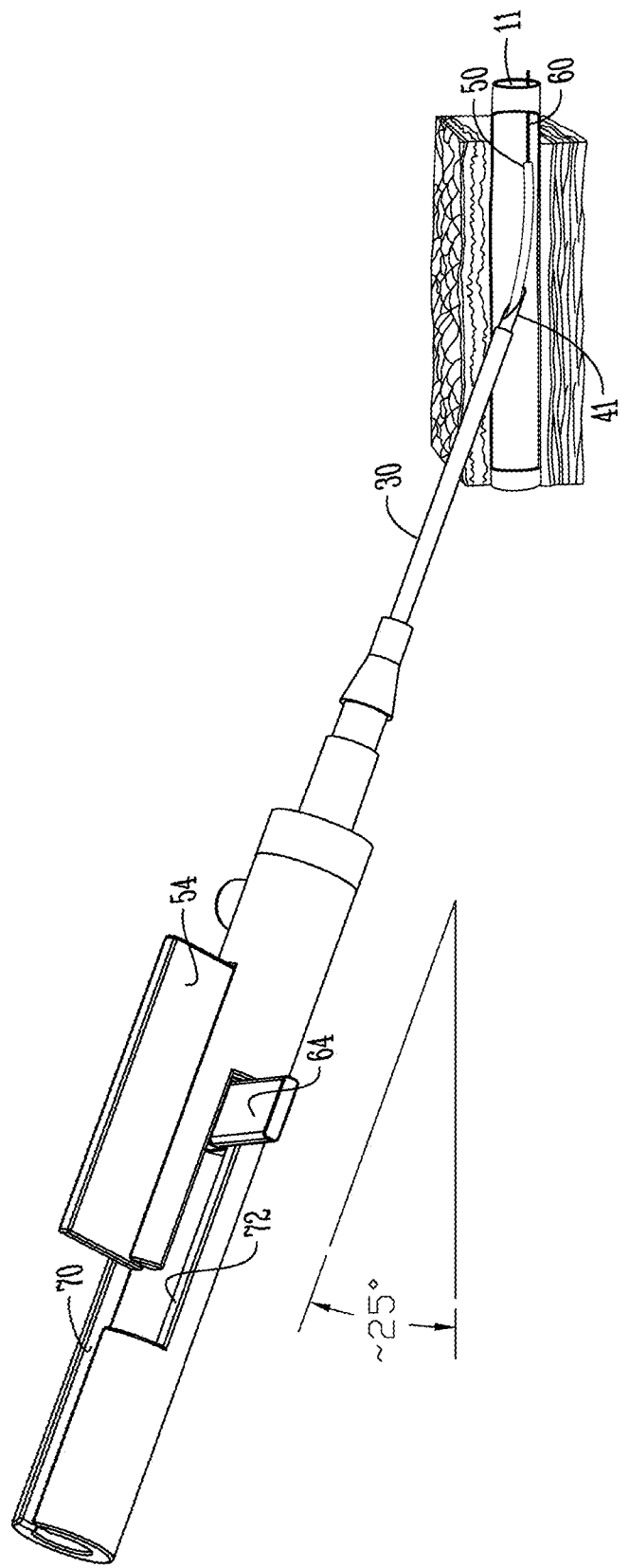
Figures 5B, 5C, 5D:
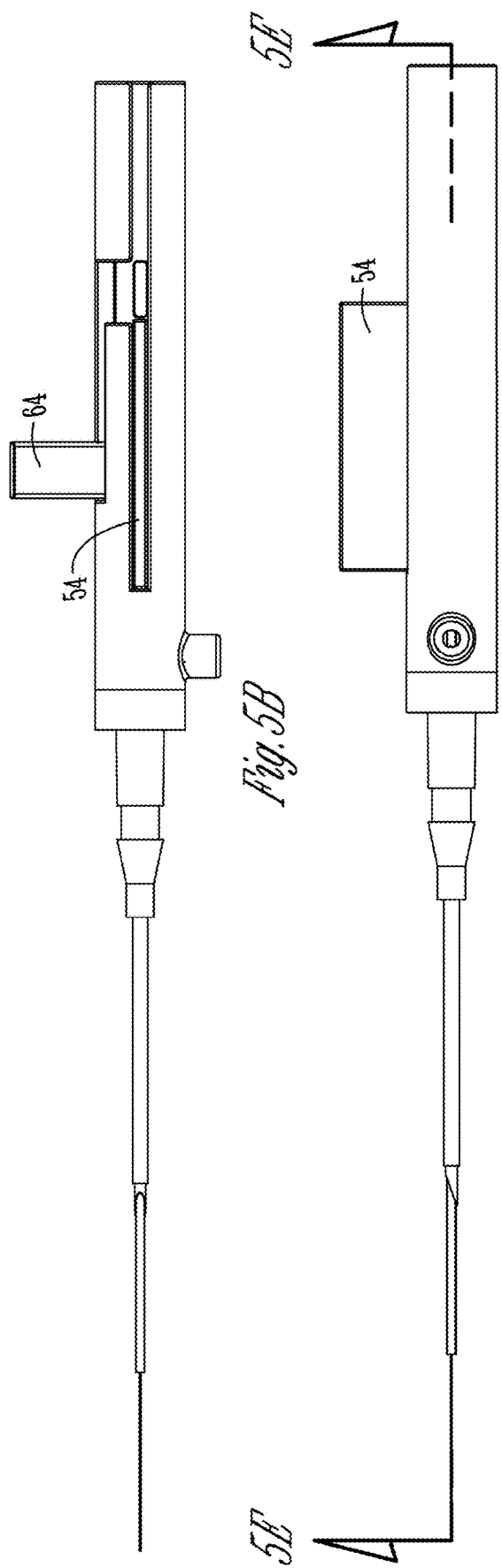
Figure 5H:
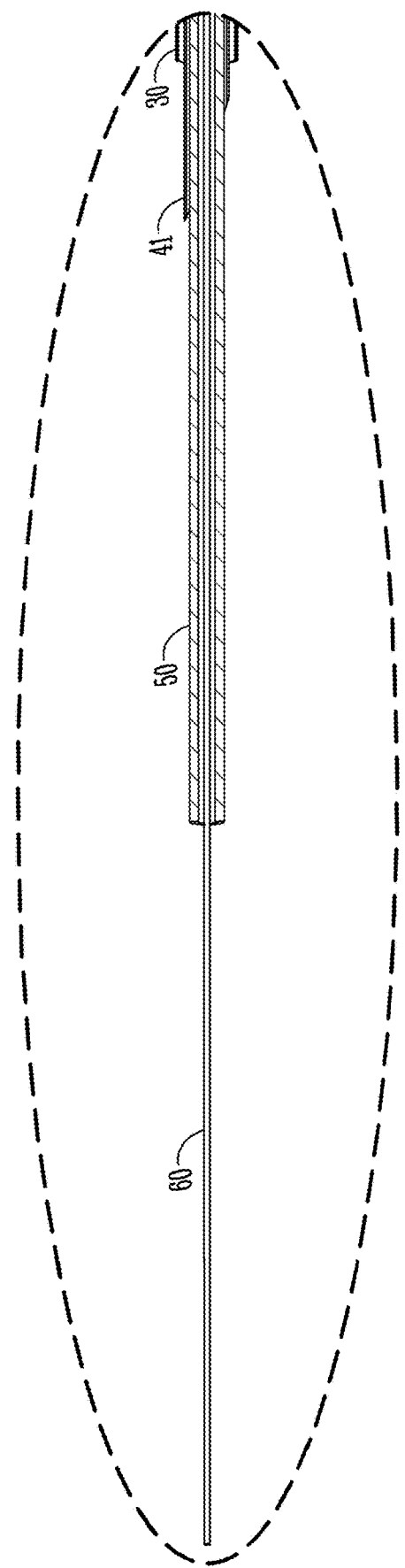
Figure 6:
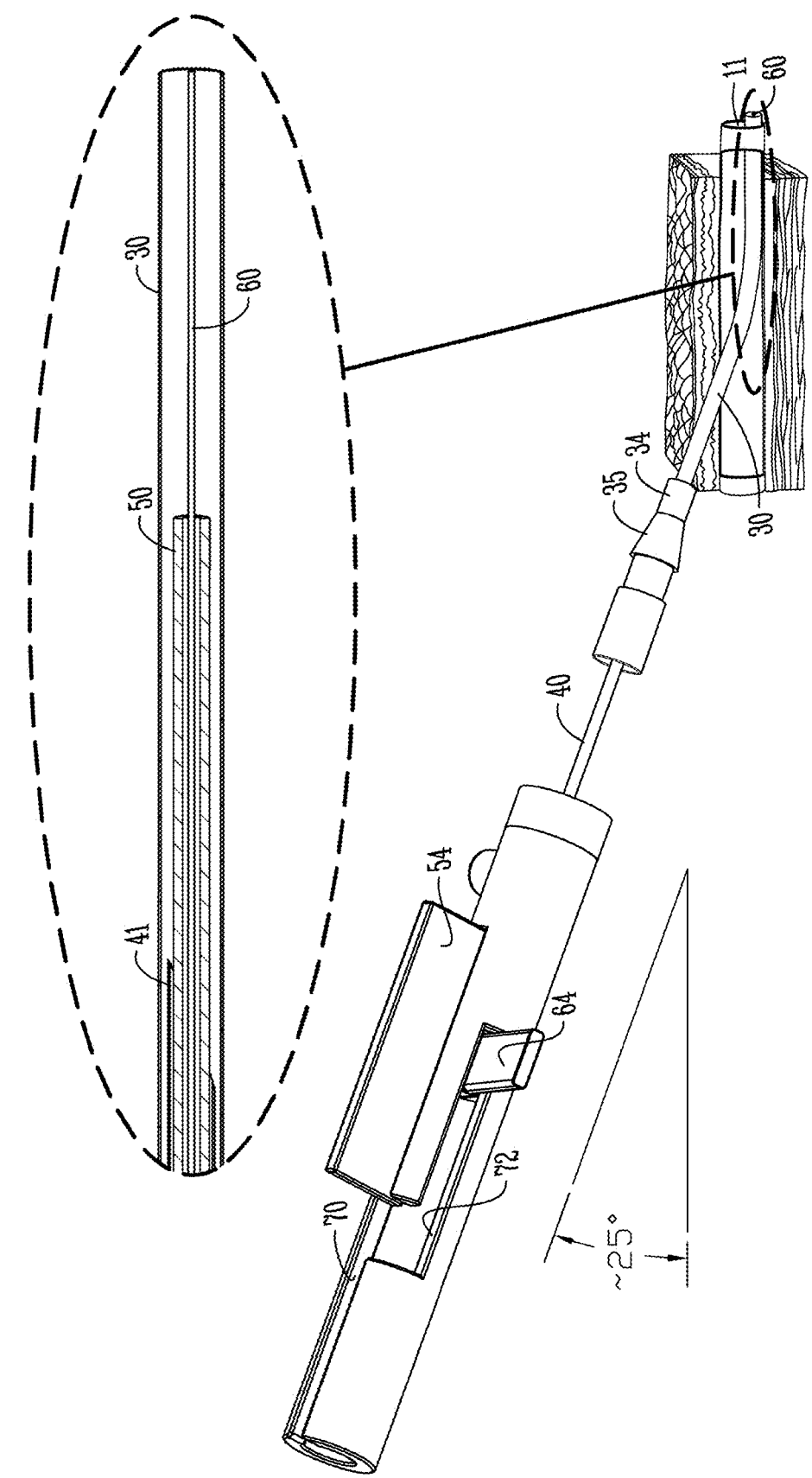
FIG. 6 is similar to FIGS. 3A, 4A, and 5A, but shows the catheter sheath moved away from the actuator handle away from its original or home position and along all of the needle, the extended portions of the stabilizing component and guide wire.

FIGS. 5A-H shows the third (fully extended) position. Slide control 64 is pushed until the end of slot 72 (which functions as a mechanical stop). As shown in FIG. 5A, guide wire 60 then extends further out of HSC tube 50 an additional distance down the blood vessel. Its flexibility receives guidance from tube 50 and tends to follow, without puncturing or leaving, the blood vessel. FIGS. 5B-5H are similar to FIGS. 4B-4H but show the second step deployment and thus the full extended deployment of both guide wire 60 and HSC 50 as well as the relationship to the internal components and positioning of slide controls 54 and 64. It is to be noted that in this example the lateral height of slider 64 is greater than the lateral or radial height of slider 54 from the longitudinal axis of apparatus 10. This helps promote the correct sequence in sliding of sliders 64 and 54. When in position 3A, the user should always push on rear-most slider 64 so sliders 64 and 54 can move together forwardly or distally in slot 70. It is to be understood, however, that the implement does allow individual and thus sequential deployment if desired.

The operator thus, with one hand or a thumb and single finger, can achieve a two-step deployment shown in FIGS. 3A, 4 and 5A. Thereafter, as indicated in FIG. 6, the user can manually push, slide, thread or otherwise manipulate the catheter sub-assembly 13 distally. The catheter cannula 30, typically a thin wall flexible tube (such as known in the art), will follow the outside of the needle and then the extended portion of HSC tube 50 and then the extended portion of guide wire 60. In this embodiment, the length of cannula 30 will be enough that it can be pushed to the end of the extended guide wire 60 while leaving a hub portion 34/35/36 outside the patient and available for connection for other use.

Figure 7:
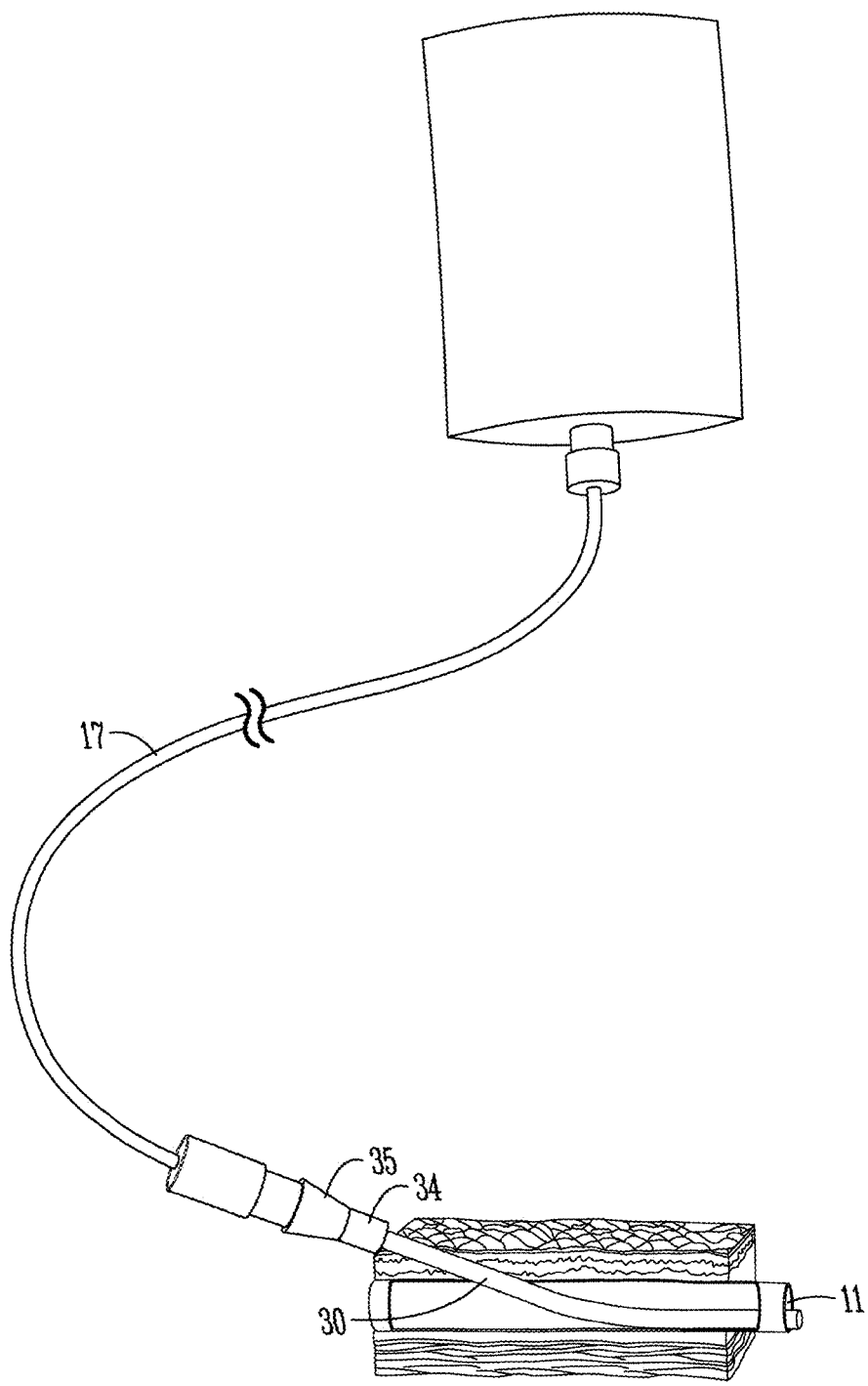
FIG. 7 is similar to FIG. 6 but shows the actuating apparatus (handle, needle, stabilizing component, and guide wire) removed from the catheter so that the catheter is left emplaced in the vein and so that the catheter can be used for any purpose.

As shown in FIG. 7, the last step would be to hold the cannula/catheter subassembly 13/30 in that slid down position but withdraw the remainder of apparatus 10. What would be left is the cannula/catheter subassembly 13/30. As can be appreciated, withdrawal of all but the catheter can proceed in a reverse order to deployment. Slider 64 would be pushed approximately in slot 72 to transition slot 71 and then behind slider 54. Then slider 54 can be pushed distally to push both back. This two-step retraction would then gently allow retrac-tion first of the more flexible and thinner guide wire 60 and then both guide wire 60 and HSC 50 back into needle 40. Then, body 20 can be moved away from the skin penetration site to withdraw the needle 40 and thus the entire assembly 10 except that catheter hub 34/35/36 would be held to leave it in its position to leave its distal end of sheath 30 in its emplaced position that had been guided out that far by the extended deployment of HSC 50 and guide wire 60.

Exemplary Embodiment Two

Figure 8A:
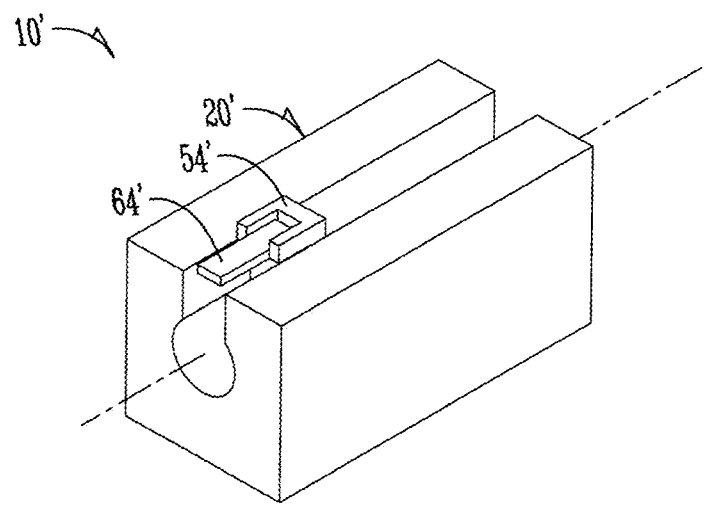
FIG. 8A is a diagrammatic illustration of a second exemplary embodiment according to the present invention.

FIG. 8A diagrammatically depicts an alternative embodiment 10' of that previously described. It utilizes a similar handle, fixed needle (not shown but would be mounted to the front of body 20' along the axis of the bore through body 20'), and deployable HSC and guide wire by slide controls on the handle. Needle 40' can be similar to needle 40 previously described. The main differences are as follows.

The U-shape slide control 54' is connected to a carriage that slides within an internal bore in handle 20'. An HSC tube 50' (the same or similar to HSC 50 previously described) is attached to slider 54'. By sliding 54' distally along handle body 20', HSC tube 50' can be moved out distally of the distal end of needle 40' or brought back inside it.

A rectangular second slider 64' has a carriage inside that same internal bore of handle 20' and is attached to guide wire 60'. It can independently extend or retract guide wire 60' by sliding action along body 30'.

Figure 8B:
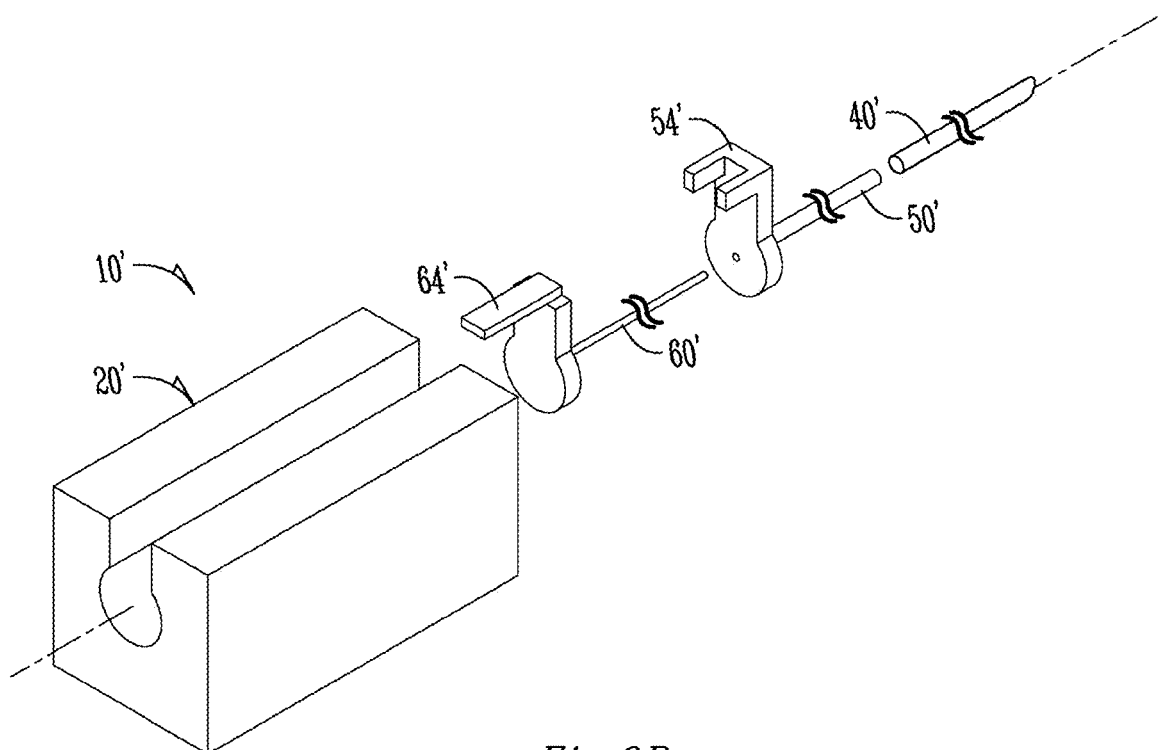
FIG. 8B shows the embodiment of FIG. 8A in a starting or home position with two manual controls on a handle in position where a hollow stabilizing member and coaxial guide wire are in retracted or home positions relative the needle and the handle.

As shown in FIG. 8B, when rectangular slide 64' is slid proximal on handle 20' and slide 54' (and basically nested around it), HSC 50' and guide wire 60' (both coaxial within tube 50') would be retracted proximally from the distal end of and into the lumen of needle 40'.

A user can step-wise deploy HSC tube 50' by selectively and independently sliding U-shaped slider 54' distally or forwardly on body 20'. There could be a mechanical stop on body 20' or otherwise (such as the end of a slot) to regulate how far forward it can go. For example, it could extend approximately the same proportional length as described regarding embodiment one.

Once rectangular slide 64' is then slid forward and nested into forwardly-slid U-shape slide 54', guide wire 60' would be deployed as a second step and beyond the distal end of deployed, extended HSC tube 50'. By the nesting relationship, slider 64' would reach a mechanical stop inside the U-shape of slider 54'.

As with embodiment one, a catheter sheath (not shown) can be preloaded on needle 40' (not shown) and utilized in a similar fashion. As can be appreciated, this is but one further example of a combination of a puncture needle and a first stabilizing hollow component that can be manually activated to deploy past the needle's distal end. It further gives but one additional example of how a second stabilizing component, in this example the guide wire 60 can further extend it. Other variations are possible.

Exemplary Embodiment Three

Figure 9A:
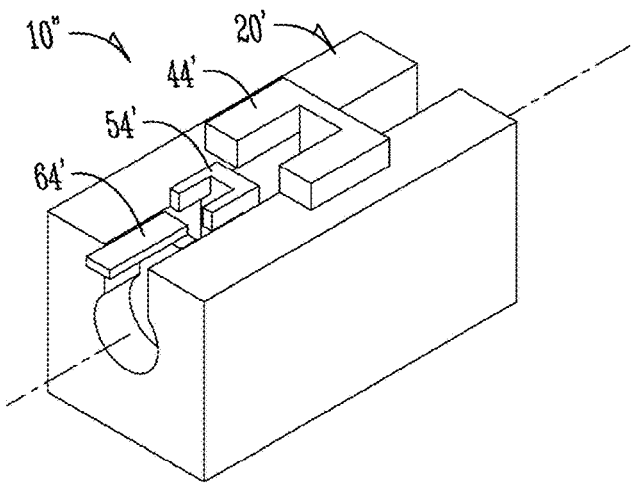
FIG. 9A is a diagrammatic view of the third exemplary embodiment according to the present invention. It is essentially the same as FIG. 8A but adds a manual control and longitudinal extendibility of a needle relative to the handle.

FIGS. 9A and B show, in similar form to FIGS. 8A and 8B, a further alternative embodiment 10" of the invention. It functions essentially like the embodiment of FIGS. 8A and 8B with the following additional feature.

This embodiment shows that further deployable and retractable members are possible. In one example, an additional slider 44' could be connected to some other type of sheath or cannula that could be slid over hollow stabilizing component 50' and selectively moved forwardly or distally. It could simply be a catheter sheath.

However, an alternative possibility exists. Second U-shaped slider 44' could be connected to a carriage that slides in the same slot/bore as the carriage portions of slider 64' and 54' of FIG. 9A. Slider 44' could have puncture needle 40' fixed to it. Thus, the additional feature of this embodiment is that needle 40' could be independently moved forward relative to handle 20'. Slider 54' (U-shaped) can also. Slider 44' can provide a mechanical stop to forward motion of slider 54'. Finally rectangular slider 64' could also be independently moved forward with slider 54' being its mechanical stop.

Each of sliders 44', 54' and 64' could likewise be moved rearwardly (proximally) along handle 20' in reverse order. In such an arrangement, guided deployment of the needle relative to the handle is possible by the finger of the operator sliding slide control 44'. One or two stabilizing components (whether or not hollow stabilizing component 50' and stabilizing wire 60') could be further extended from resulting position of needle 40'.

This would also align with the optional possibility that the needle could be attached to either the rear-most slider 64' or middle slider 54'. As previously mentioned, at least one of the stabilizing components could potentially be slid over the needle and outwardly. Any catheterization sheaths would then be loaded on that outermost stabilizing component that slid outward to its final position. A slideable needle would require design of relative length and position of each of slideable needle 40', HSC 50' and guide wire 60' and their respective slide controls 44', 54', and 64' so that once needle 40' is fully extended, HSC 50' could be extended beyond it, and that wire 60' could be extended beyond HSC 50'.

Optionally, housing 20 or 20' could include features that would keep the entire device 10, 10' or 10" in a home or starting position. For example, some sort of cap, bracket, retainer, or the like could be placed over the proximal end of body 20 or 20' to prevent any of the components from sliding out the end regardless of its orientation of handle 20 or 20'. Similarly, some sort of a cap, retainer, or otherwise could be placed over the distal end of the needle to prevent any of the extendible members from extending until that member is removed or released. Still further, packaging of an assembled apparatus 10 could hold all the elements in that starting position. Once the packaging is removed, it is then manipulatable as described.

Further features of the embodiment 10" of FIGS. 9A and B are set forth below. Some or all can be applied in analogous fashion to embodiments 10 and 10'.

A method for incorporating a guide wire device into a peripheral intravenous catheter is described herein. The method embodies three specific steps that incorporate the Seldinger technique of using a support system within the vein to support the catheter, while circumventing the described limitations. Each step will be represented by a relevant feature of the specially designed catheter device 10". First, a needle will be used to pierce through the vein and establish one level of support. Next, a small, thin hollowed tube, referred to as the hollow stabilizing component ("HSC"), will be directed through the needle in the same manner as the arterial catheter guide wire to provide a second layer of support not found in the usual Seldinger technique. The HSC will be shorter than the normal guide wire, but still long enough so that it can be easily moved a distance past the inserted needle into the targeted vein. The HSC must be small enough to fit within 18-22 gauge needles, as well as lesser-used gauge sizes. The final step involves a guide wire element that can fit within the HSC and be extended further into the vein from the HSC tube's opening. This final guide wire, referred to as a thin stabilizing guide wire, will be made of a material that can support the weight of the catheter as it is slid over the three components. A stabilizing guide wire made from durable metal machined to the appropriate length and diameter to fit within the HSC while being rigid enough to support the catheter sheath may be utilized, yet we must be cautious with a metal guide wire due to the thin nature of vein walls. Alternate materials with similar strength properties may be used as well. The peripheral venous sheath would then be slid into the vein over the hollow stabilizing component and subsequently the thin stabilizing guide wire. Like the arterial catheter, once the sheath has been installed, all three stabilizing components (needle, HSC, thin stabilizing guide wire) would be easily removed, leaving the catheter fixed in the vein. As will be appreciated by those skilled in the art, any of the apparatus described herein could be utilized with a guide wire 60 that is not metal. The Seldinger technique conventionally uses a metal guide wire. On the other hand, use of a metal guide wire is not precluded with these embodiments.

Figure 9B:
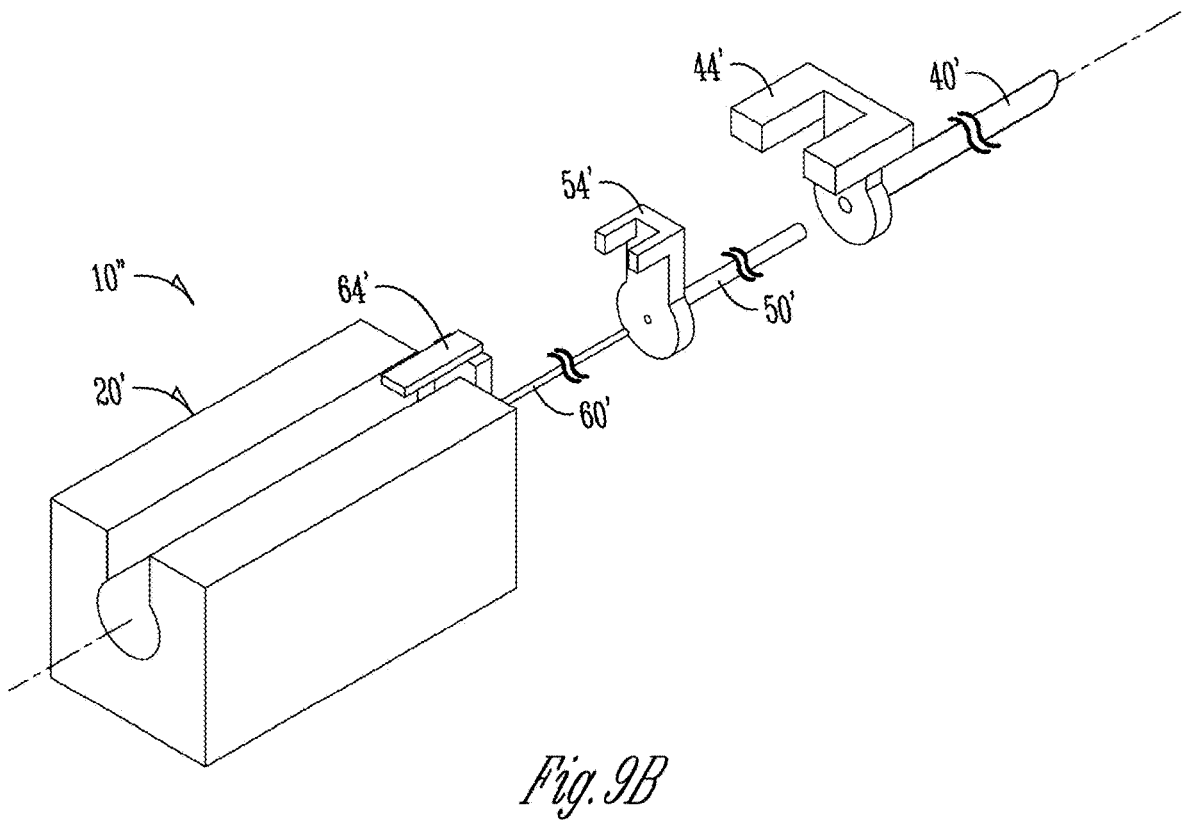
FIG. 9B is a partially exploded view of the embodiment of FIG. 9A showing extension of the hollow stabilizing component and guide wire from a longitudinally moveable needle.

FIGS. 9A and 9B show perspective views of the assembled catheter assembly 10" with a segmented stabilization system. The catheter assembly is used primarily, but not exclusively, in accessing peripheral veins and arteries for the administration of various drugs and fluids. The present method allows deployment of the catheter components by one operator. The catheter of the present method allows a catheter to pass over a stable shaft that is segmented in order to preserve the integrity of the accessed vessel. The catheter assembly includes an outer housing 20' with an interior containing a catheter (not shown), a needle assembly 40'/44', an HSC assembly 50'/54', and a thin stabilizing guide wire assembly 60'/64'. The outer housing 20' may be made of plastic, acetal, or other materials known in the art. The outer housing 20' has a housing hollow which can contain all necessary sliding assemblies. The catheter assembly remains in a constrained position until the operator, who is most often a physician or registered nurse, takes action. After performing standard preparatory procedures well known in the art, the operator first performs step one, piercing the vessel with the needle 40'. This is done by the operator pushing needle deployment piece 44' forward with one or a number of fingers. Needle 40' is usually of a gauge size between 18 and 22. Next, the operator performs the second step, passing HSC 50' through needle 40'. This step is performed by the operator pushing the HSC deployment piece 54' forward with one or a number of fingers. Guide wires are frequently used to navigate vessels before catheter sheaths are passed over said guide wires, but the HSC 50' hollow design provides support and guidance for the actual guide wire. Likewise, said hollow design allows for the third step performed by the operator. In the third step, the operator pushes forward the thin stabilizing guide wire deployment piece 64' with one or a number of fingers to pass the thin stabilizing guide wire 60' through the HSC 50', extending the thin stabilizing guide wire 60' past the HSC 50' and into the vessel. Thin stabilizing guide wire 60' may be one of a plurality of materials. Each possible material must be strong enough to support the passage of the catheter sheath over it. In an exemplary embodiment of the present invention, the thin stabilizing guide wire 60' may be highly flexible until it is exposed to the temperature of human blood for a specific period of time. One material could be nitinol which is configured to increase rigidity upon exposure to temperatures on the order of in vivo human blood. After exposure for said specific period of time, the material may become more rigid. These properties would allow the thin stabilizing guide wire 60' to easily pass through fragile vessels without damaging vessel walls. Then, once the operator advances the thin stabilizing guide wire 60' to its desired location by pushing the thin stabilizing guide wire deployment piece 64', the thin stabilizing guide wire 60' would become rigid enough to support a catheter sheath.

In another exemplary embodiment, the thin stabilizing guide wire 60' may be made of a swellable polymer. Such a material would allow the thin stabilizing guide wire 60' to be thin and rigid in a dry state. The material would then increase in diameter with exposure to a solution such as human blood. In the present invention, the swellable polymer would be rigid when initially traveling through the first vessel wall, so the wall may be pierced, but flexible enough not to punch through the second, opposing wall of the vessel. Over a specific period of time, the swellable polymer would increase in diameter to match the diameter of the HSC 50', which would be substantial enough for a catheter to pass over it in the right location. The specific period of time would be such that the operator would have enough time to position the thin stabilizing guide wire 60' in the desired location.

While the thin stabilizing guide wire 60' may be made of metal or a swellable polymer as in the exemplary embodiments, it is not constrained to only those materials. The thin stabilizing guide wire 60' may be a material that does not change properties at all when coming into contact with human blood. It may simply be a machined metal or polymer with just enough rigidity and strength as to not damage vessel walls but still allow a catheter to pass over it in a secure and stable manner. Likewise, the polymer would have a high enough modulus of elasticity that it will not break during normal use even at the small diameters required. One example would be radiopaque polyurethanes, which have been used extensively in catheter designs. Any material used in the thin stabilizing guide wire 60', as in any component of the catheter assembly with a segmented stabilization system, will be safe for contact within the human body. Furthermore, any material used as the thin stabilizing guide 60' wire may be coated with a material that facilitates its passage through the HSC 50' and into the blood vessel without swelling to an extent to occlude the vessel thereby preventing the sliding of the catheter over the thin stabilizing guide wire 60'.

Such a material may be, but is not limited to, a polymer such as mannose. The HSC 50' may also be coated with such a material to facilitate its passage through the needle 40' and into the blood vessel. To further facilitate the easy sliding of assembly components, tolerances well known in the art must be maintained to ensure a sliding, not sticking fit between the HSC 50', thin stabilizing guide wire 60', and needle 40'.

Figure 2:
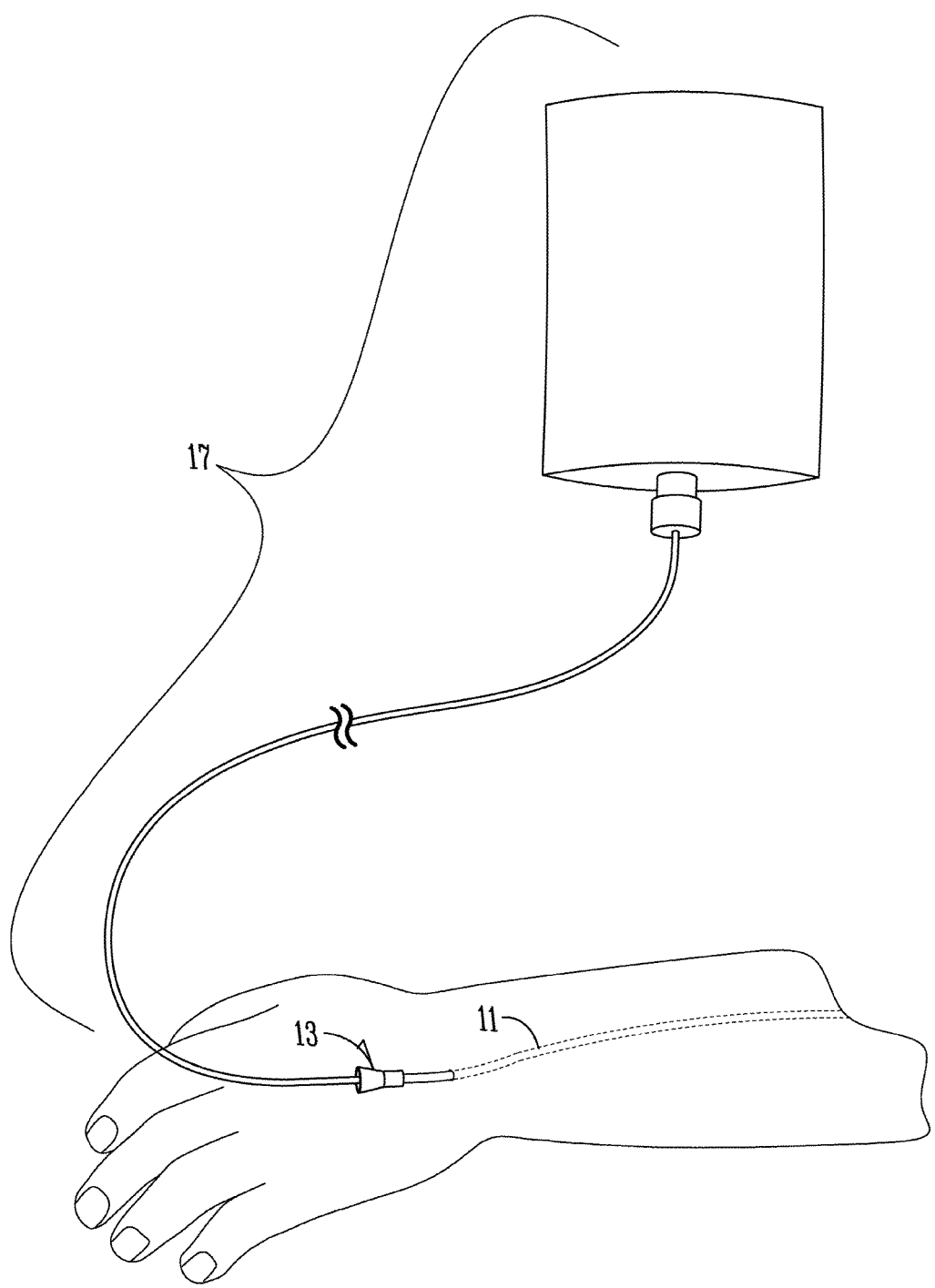
FIG. 2 is a highly diagrammatic view of the catheter of FIG. 1A placed in a peripheral vein of a patient and connected to either an output or input storage bag or container via a tubular connection.

Once the operator has deployed the thin stabilizing guide wire 60', the segmented stabilization system is in position within the patient's vessel. The segments are made up of the needle 40', the HSC 50', and the thin stabilizing guide wire 60'. The thin stabilizing guide 60' wire passes through the HSC 50', which passes through the needle 40'. In addition, the tip of the thin stabilizing guide wire 60' should be a blunted, bullet-like tip to prevent vein puncture through both sides of the vessel. Each component remains anchored within the outer housing 20' of the catheter assembly so no component could break free and travel farther into the patient's vessel than intended. By entering the vessel in a step-wise manner, sudden and forceful movements that may puncture a vessel wall are avoided. The multi-step progression allows the operator to an innovative method for performing the final step, sliding the catheter sheath over the segmented stabilization system and facilitating the administration of an intravenous catheter into the patient's vessel, as shown in FIG. 2. FIG. 1A illustrates how, prior to administration of the catheter assembly, the catheter sheath can be positioned so that it faces the handle 20' and covers the base of the needle 40' leaving the sharp tip of the needle protruding out. The base of the catheter sheath is fitted on the needle so that it is secure when administering the needle 40' and the segmented stabilization system into the patient's vessel. As known in the art, a portion of the needle 40' is extended from the catheter sheath to facilitate insertion into the vessel of the patient as illustrated in FIG. 3A. The tip of the catheter sheath rests above the insertion as the needle tip punctures and enters the vessel. The catheter sheath tip would be bevel shaped to allow for the catheter sheath to enter the vessel more easily and decrease the risk of pushing the assembly out of the vein as the catheter sheath is advanced. Likewise, the beveled tip of the catheter sheath facilitates insertion into the vessel over the segmented stabilization system. The base of the catheter sheath is standard with the prior art and can be fitted with standard mechanisms such as a Luer lock or others. Furthermore, the catheter may/should be made of a more flexible material than currently used in the art of cannulation to allow for easier threading into tortuous, small veins. Because the segmented stabilization system is in place, the catheter sheath, which would be difficult to navigate a vessel independently, easily follows the correct path of the vessel.

It is understood that the various components of the catheter assembly 10" with the segmented stabilization system may be coated by a material that allows easier passage through another component or into the vessel. Such coatings may act as a lubricant to facilitate entrance into the patient's vessel. Various barriers may also be in place to prevent the thin stabilizing guide wire 60' from contacting human blood before the appropriate time. For example, the thin stabilizing guide wire 60' may have to pass through a thin wall to enter the vessel so that blood does not prematurely cause the thin stabilizing component 60' to reach its final rigidity.

Once the catheter is passed over the segmented stabilizing system, the segmented stabilizing system and its associated assemblies are withdrawn from the patient's body, leaving only the catheter sheath in the vessel. Withdrawing the segmented stabilizing system may be achieved by the operator performing the reverse order of the operations that put the HSC 50' and thin stabilizing guide wire 60' in place. This means that in an exemplary embodiment, the needle deployment piece 44', HSC deployment piece 54', and thin stabilizing guide wire deployment piece 64' are all pulled back by one or a number of fingers of the operator to withdraw the thin stabilizing guide wire 60', HSC 50', and needle 40'. Alternatively, a separate mechanism may be deployed to remove the segmented stabilizing system. Once the segmented stabilizing system is removed, the catheter sheath is clear of obstructions and may remain in the patient's peripheral vessel for a period of time sufficient for all necessary drugs and/or fluids to be administered to the patient. The catheter sheath must be of sufficient length for the volume of fluid and/or drugs to be administered. It must also be of sufficient diameter to allow the timely administration of said drugs and/or fluids.

In an exemplary embodiment, the length of the portion of thin stabilizing guide wire 60' extending outside extended HSC 50' is 1 inch, and the diameter of the thin stabilizing guide wire 60' is 0.04 inch. It is appreciated that the thin stabilizing guide wire deployment piece 64' may take a variety of different shapes, and that each component of the thin stabilizing guide wire assembly may be made of materials known in the art.

The HSC assembly incorporates an HSC 50', and an HSC deployment piece 54'. Connection between the two pieces may be by medical grade glue or other means known in the art. In one exemplary embodiment, the outer diameter of the HSC 50' is 0.08 inch and the inner diameter is 0.04 inch. The length of the HSC 50' is 0.70 inch. It is appreciated that the HSC deployment piece 54' may take a variety of different shapes, and that each component of the HSC assembly may be made of materials known in the art.

The needle assembly includes a needle 40', and a needle deployment piece 44'. In an exemplary embodiment, needle 40' is 0.50 inches long, with an outer diameter of 0.13 inch and an inner diameter of 0.08 inch. The needle 40' may have a beveled tip to facilitate insertion. It is appreciated that each component of the needle assembly may be made of a variety of materials known in the art. It is also appreciated that all sizes of exemplary embodiments may be scaled depending on the specific application of the catheter.

Options and Alternatives

It will be appreciated that the invention can take many forms and embodiments. Variations obvious to those skilled in the art will be included within the invention which is defined solely by the claims. Some of those options and alternatives have been described previously. Below are some additional examples.

For example, the size, shape, configuration, and materials for various components of the invention can vary according to the desire.

Another example would be that deployment mechanisms or actuators could be different for extension deployment versus retraction. In the described embodiments they are the same. As mentioned, one application is intravascular catheterization. However, any subsequent placement of some sort of a sheath or cannula may be possible. Additionally, the invention may have other uses beyond those.

It is also to be understood that in one embodiment, a hollow or tubular stabilizing component is deployable beyond distal end of a puncture needle. This hollow or tubular stabilizing component may provide a guide for a guide wire. It also could provide a guide for a further tubular or hollow stabilizing component deployable beyond the fully extended distal end of the first hollow stabilizing component. Because the first hollow stabilizing component is hollow, it can have other potential features or uses. Furthermore, any of those extendible or deployable stabilizing components can be concentric relative to each other in the sense that one or more can be slidable along the puncture needle or over it. There can be more than one and more than two additional extendible stabilizing components.

Furthermore, in the embodiments having a guide wire inside a hollow stabilizing component, they do not have to be deployed together. Additionally, the guide wire does not necessarily have to then be deployed before catheter sheath is placed. The operator could decide that utilization of the first hollow stabilizing component is sufficient. As described above, the slider 64 or other deployment control could be left alone and only the hollow stabilizer component control utilized for that purpose. Still further, the user could decide to deploy in a first step both hollow stabilizing component 50 and internal wire 60 so they both are extended from the needle as in FIG. 4E. The operator could then decide a further second step extension of wire 60 is not needed.

A further example, the relative extendible lengths of any stabilizing component or components can be matched to at least the approximate length of the sheath 30 which will be guided over it or them. But they do not have to be of equal or even correlated length. For example, full extended HSC 50 and wire 60 could be longer than the reach of catheter sheath 30 when pushed forwardly. Or they could be shorter. However, it has been found it could be beneficial that sheath 30 length is at least approximately equal to combined length of the fully extended HSC 50 and wire 60. This gives confidence to the user that there would be the supplemental stabilization assistance and guidance to approximately the same extended position from the distal end of the needle as the sheath length.

Several examples of coatings or additions to the components have been described. Others may be possible.

It has been found that a stabilizing component, at least a second stabilizing component and especially if in wire form, would have more flexibility than typical metal guide wires such as are conventional with the Seldinger technique. Use of the term "wire" herein is intended to not be limited to metal. One example of higher flexibility wire is plastic. An example has been given. It could be multi-filament, twisted, or composite, instead of monofilament. Other materials and configurations are possible.

Several of the embodiments have an integrated apparatus 10. It is to be understood that there could be forms where the deployment mechanisms are not specifically integrated with the components to place the catheter. It will be understood that this disclosure, in many respects, is only illustrative. Changes may be made in details, particularly in matters of shape, size, material, and arrangement of parts.

What is claimed is:
1. An apparatus designed for facilitating subcutaneous insertion of a catheter comprising:
   a. a hollow needle assembly comprising a hollow needle having a longitudinal axis and a distal end; and
   b. a hollow stabilizing component assembly comprising a hollow stabilizing component having a longitudinal axis and a distal end, the hollow stabilizing component coaxial to and selectively movable between a retracted position along the longitudinal axis of the needle to a deployed fully extended position extended past the distal end of the needle;
c. so that the needle can be used for subcutaneous access and the hollow stabilizing component can provide a first support and guide section extendible from the needle;
d. further comprising an additional stabilizing component selectively movable between a retracted position along the longitudinal axis at the hollow stabilizing component to a deployed fully extended position extended from the distal end of the hollow stabilizing component so that the needle can be used for subcutaneous access, the hollow stabilizing component providing a first support and guide section extendible from the needle, and the additional stabilizing component providing a second support and guide section extendible from the needle: wherein the additional stabilizing component comprises a guide wire;
e. further comprising a handle to which is mounted the hollow needle assembly and a hollow stabilizing component deployment device attached to and for manual movement of the hollow stabilizing component over a first range and a guide wire deployment device attached to and for manual movement of the guide wire over the first range and a second range, where the hollow stabilizing component is slidable inside the needle and the guide wire is slidable inside the hollow stabilizing component; wherein the hollow stabilizing component and guide wire deployment devices comprise sliding carriages that can be manually moved by a user by a manually-operable control;
wherein the manually-operable control moves the sliding carriages of the hollow stabilizing component and guide wire deployment devices in a slot system, the slot system allowing:
   i. longitudinal movement of the manually-operable control for a first distance along the slot system to move the hollow stabilizing component from its fully retracted to its deployed fully extended position;
   ii. transition movement of the control for a second distance along the slot system; and
   iii. longitudinal movement of the control for a third distance along the slot system to move the stabilizing guide wire to its deployed fully extended position beyond the distal end of the extended hollow stabilizing component.

2. The apparatus of claim 1 wherein the guide wire comprises plastic.

3. The apparatus of claim 2 wherein the guide wire has a degree of flexibility on the order of plastic fishing line.

4. The apparatus of claim 1 further comprising a catheter sheath positioned on and covering a portion of the needle proximal to the distal end of the needle in a home position, the catheter sheath being selectively slideable along and off of the needle including when at least the hollow stabilizing member is in extended position.

5. The apparatus of claim 1 further comprising a catheter sheath positioned on and covering a portion of the needle proximal to the distal end of the needle in a home position, the catheter sheath being selectively slideable along and off of the needle wherein cumulative length of the hollow stabilizing component and the additional stabilizing component in extended positions is approximately equal to a length of the catheter sheath.

6. The apparatus of claim 1 wherein the needle is a substantial rigid peripheral venous catheterization needle, the hollow stabilizing component has a degree of flexibility and slides along but is slightly spaced from the needle, and the stabilizing guide wire has a degree of flexibility and slides through the hollow stabilizing component.

7. The apparatus of claim 1 further comprising a flash chamber at a proximal end of the needle through which the hollow stabilizing component passes and which is in fluid communication with the space between the hollow stabilizing component and the needle so that collection of blood in the chamber is indicative of proper emplacement of the apparatus in a peripheral vein.

8. The apparatus of claim 7 further comprising a transparent or translucent portion of or in fluid communication with the flash chamber to allow visual confirmation of blood being collected in the chamber.

9. The apparatus of claim 1 wherein the needle, hollow stabilizing component, and guide wire form a step-wise deployable and retractable, segmented stabilization system.

10. The apparatus of claim 1 further comprising a retainer to retain the hollow stabilizing component relative the needle.

11. The apparatus of claim 9 wherein each of the needle, hollow stabilizing component, and guide wire are slideable in the handle to allow selective stepwise deployment, one past the other, of the needle, then the hollow stabilizer component, and then the stabilizing guide wire sequentially from nested retracted positions to individual fully extended positions.

12. The apparatus of claim 1 wherein the hollow stabilizing component and the guide wire comprise a plastic material with a degree of flexure.

13. The apparatus of claim 1 wherein the stabilizing guide wire is made of a material that becomes sufficiently rigid to stabilize the catheter's insertion when the material is exposed to the temperature of human blood.

14. The apparatus of claim 13 wherein the material is nitinol.

15. The apparatus of claim 13 wherein the material comprises swellable polymer that increases outside diameter when exposed to the temperature of human blood.

16. The apparatus of claim 1 further comprising a material on the exterior of at least one of the hollow stabilizing component and guide wire adapted to promote smooth movement relative to other components.

17. The apparatus of claim 16 wherein the material comprises a polymer.

18. The apparatus of claim 17 wherein the polymer comprises mannose.

19. The apparatus of claim 1 wherein the slot arrangement is in the handle.

20. The apparatus of claim 1 wherein the slot arrangement is in one or more of the deployment devices.

21. The apparatus of claim 1 wherein the slot arrangement is in one or more of the handle and one or more of the deployment devices.

22. An apparatus designed for facilitating subcutaneous insertion of a catheter comprising:
a. a hollow needle assembly comprising a hollow needle having a longitudinal axis and a distal end; and
b. a hollow stabilizing component assembly comprising a hollow stabilizing component having a longitudinal axis and a distal end, the hollow stabilizing component coaxial to and selectively movable between a retracted position along the longitudinal axis of the needle to a deployed fully extended position extended past the distal end of the needle;

c. so that the needle can be used for subcutaneous access and the hollow stabilizing component can provide a first support and guide section extendible from the needle;

d. further comprising an additional stabilizing component selectively movable between a retracted position along the longitudinal axis of the hollow stabilizing component to a deployed fully extended position extended from the distal end of the hollow stabilizing component so that the needle can be used for subcutaneous access, the hollow stabilizing component providing a first support and guide section extendible from the needle, and the additional stabilizing component providing a second support and guide section extendible from the needle; wherein the additional stabilizing component comprises a guide wire;

e. further comprising a handle to which is mounted the hollow needle assembly and a hollow stabilizing component deployment device attached to and for manual movement of the hollow stabilizing component over a first range and a guide wire deployment device attached to and for manual movement of the guide wire over a second range, where the hollow stabilizing component is slidable inside the needle and the guide wire is slidable inside the hollow stabilizing component; wherein the hollow stabilizing component and guide wire deployment devices comprise sliding carriages that can be manually moved by a user by a manually-operable control;

wherein the manually-operable control moves the sliding carriages of the hollow stabilizing component and guide wire deployment devices in a slot system, the slot system allowing:

i. longitudinal movement of the manually-operable control for a distance along the slot system to together move the hollow stabilizing component and the guide wire over the first range from the retracted positions to the deployed fully extended position for the hollow stabilizing component beyond the distal end of the needle; and ii. longitudinal movement of the control for an additional distance along the slot system to independently move the stabilizing guide wire over the second range to its deployed fully extended position beyond the distal end of the extended hollow stabilizing component.

23. The apparatus of claim 22 wherein the sliding carriages are longitudinally spaced apart farther when both the hollow stabilizing component and the guide wire are fully retracted, and closer together when the hollow stabilizing component if moved to its extended position and the guide wire is moved to its extended position.

24. The apparatus of claim 22 wherein the manually-operable control to move the sliding carriages of the hollow stabilizing component and guide wire deployment devices in the slot system further allowing:

i. reverse longitudinal movement of the control along the additional distance along the slot system to independently move the stabilizing guide wire over the second range to from its deployed fully extended position beyond the distal end of the extended hollow stabilizing component to a partially retracted position in the hollow stabilizing component; and ii. reverse longitudinal movement of the manually-operable control along the distance along the slot system to together move the hollow stabilizing component and the guide wire over the first range from the deployed fully extended position for the hollow stabilizing component beyond the distal end of the needle to the retracted position.

\* \* \* \* \*